(12) United States Patent
Chavez et al.

(10) Patent No.: US 12,329,602 B2
(45) Date of Patent: Jun. 17, 2025

(54) MODULAR FABRICATION OF DENTAL APPARATUSES

(71) Applicant: Align Technology, Inc., San Jose, CA (US)

(72) Inventors: Jennifer Chavez, Fremont, CA (US); Peter Webber, San Jose, CA (US); Peter Dorfinger, Los Altos Hills, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/498,736

(22) Filed: Oct. 11, 2021

(65) Prior Publication Data

US 2022/0110718 A1  Apr. 14, 2022

Related U.S. Application Data

(60) Provisional application No. 63/090,092, filed on Oct. 9, 2020.

(51) Int. Cl.
| | |
|---|---|
| *A61C 7/10* | (2006.01) |
| *A61C 7/00* | (2006.01) |
| *A61C 7/08* | (2006.01) |
| *A61C 7/16* | (2006.01) |
| *B29C 64/386* | (2017.01) |

(Continued)

(52) U.S. Cl.
CPC ............... *A61C 7/10* (2013.01); *A61C 7/002* (2013.01); *A61C 7/08* (2013.01); *A61C 7/16* (2013.01); *B29C 65/48* (2013.01); *B33Y 40/20* (2020.01); *B33Y 80/00* (2014.12); *G16H 20/40* (2018.01); *A61C 2201/00* (2013.01); *B29C 64/386* (2017.08); *B29L 2031/753* (2013.01); *B33Y 50/00* (2014.12)

(58) Field of Classification Search
CPC .. A61C 7/10; A61C 7/08; A61C 7/002; A61C 7/00; A61C 87/00; A61C 7/16; B29C 64/336; B29C 64/124; B33Y 40/20; B33Y 80/00; B33Y 70/00; B33Y 70/10
See application file for complete search history.

(56) References Cited

U.S. PATENT DOCUMENTS

| | | |
|---|---|---|
| 5,820,368 A | 10/1998 | Wolk |
| 6,183,248 B1 | 2/2001 | Chishti et al. |

(Continued)

OTHER PUBLICATIONS

Ultrasonic welding; Azo Materials; retrieved from the internet (https://www.azom.com/article.aspx?ArticleID=119); Feb. 27, 2001; 5 pages.

*Primary Examiner* — Heidi M Eide
*Assistant Examiner* — Lina Faraj
(74) *Attorney, Agent, or Firm* — Shay Glenn LLP

(57) ABSTRACT

Methods of forming dental apparatuses, such as palatal expanders. Methods may include photopolymerizing a palatal region and left and right tooth engagement regions of a palatal expander. Junction regions coupling the palatal region and left and right tooth engagement regions may be formed using different combinations of first and second photo-curable materials in a layer-by-layer fashion such that each layer has a different ratio of first and second polymer materials. This can provide gradual material transitions and a robust bond between the palatal region and each of the left and right tooth engagement regions.

15 Claims, 24 Drawing Sheets

(51) Int. Cl.
  *B29C 65/48*  (2006.01)
  *B29L 31/00*  (2006.01)
  *B33Y 40/20*  (2020.01)
  *B33Y 50/00*  (2015.01)
  *B33Y 80/00*  (2015.01)
  *G16H 20/40*  (2018.01)

(56) References Cited

U.S. PATENT DOCUMENTS

| | | |
|---|---|---|
| 6,210,162 B1 | 4/2001 | Chishti et al. |
| 6,309,215 B1 | 10/2001 | Phan et al. |
| 6,386,864 B1 | 5/2002 | Kuo |
| 6,454,565 B2 | 9/2002 | Phan et al. |
| 6,471,511 B1 | 10/2002 | Chishti et al. |
| 6,497,574 B1 | 12/2002 | Miller |
| 6,524,101 B1 | 2/2003 | Phan et al. |
| 6,572,372 B1 | 6/2003 | Phan et al. |
| 6,607,382 B1 | 8/2003 | Kuo et al. |
| 6,705,863 B2 | 3/2004 | Phan et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,947,038 B1 | 9/2005 | Anh et al. |
| 6,957,118 B2 | 10/2005 | Kopelman et al. |
| 6,976,627 B1 | 12/2005 | Culp et al. |
| 7,074,039 B2 | 7/2006 | Kopelman et al. |
| 7,092,784 B1 | 8/2006 | Simkins |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 * | 3/2007 | McSurdy, Jr. ............ A61C 7/10 433/24 |
| 7,220,124 B2 | 5/2007 | Taub et al. |
| 7,236,842 B2 | 6/2007 | Kopelman et al. |
| 7,245,977 B1 | 7/2007 | Simkins |
| 7,261,533 B2 | 8/2007 | Wrosz et al. |
| 7,335,024 B2 | 2/2008 | Wen |
| 7,347,688 B2 | 3/2008 | Kopelman et al. |
| 7,354,270 B2 | 4/2008 | Abolfathi et al. |
| 7,384,266 B2 | 6/2008 | Wen |
| 7,435,084 B2 | 10/2008 | Liu et al. |
| 7,448,514 B2 | 11/2008 | Wen |
| 7,472,789 B2 | 1/2009 | Wu et al. |
| 7,476,100 B2 | 1/2009 | Kuo |
| 7,481,121 B1 | 1/2009 | Cao |
| 7,481,647 B2 | 1/2009 | Sambu et al. |
| 7,543,511 B2 | 6/2009 | Kimura et al. |
| 7,553,157 B2 | 6/2009 | Abolfathi et al. |
| 7,600,999 B2 | 10/2009 | Knopp |
| 7,604,181 B2 | 10/2009 | Culp et al. |
| 7,641,828 B2 | 1/2010 | DeSimone et al. |
| 7,648,360 B2 | 1/2010 | Kuo |
| 7,658,610 B2 | 2/2010 | Knopp |
| 7,674,422 B2 | 3/2010 | Kuo |
| 7,711,447 B2 | 5/2010 | Lu et al. |
| 7,748,199 B2 | 7/2010 | Sankaran et al. |
| 7,766,658 B2 | 8/2010 | Tricca et al. |
| 7,771,195 B2 | 8/2010 | Knopp et al. |
| 7,802,987 B1 | 9/2010 | Phan |
| 7,819,659 B2 | 10/2010 | Wen |
| 7,831,322 B2 | 11/2010 | Liu et al. |
| 7,840,373 B2 | 11/2010 | Culp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,922,490 B2 | 4/2011 | Wen |
| 7,947,508 B2 | 5/2011 | Tricca et al. |
| 7,957,824 B2 | 6/2011 | Boronvinskih et al. |
| 8,019,465 B2 | 9/2011 | Spiridonov et al. |
| 8,030,588 B2 | 10/2011 | Culp et al. |
| 8,087,932 B2 | 1/2012 | Liu |
| 8,152,518 B2 | 4/2012 | Kuo |
| 8,172,569 B2 | 5/2012 | Matty et al. |
| 8,201,560 B2 | 6/2012 | Dembro |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,414,291 B1 | 4/2013 | Jamilian et al. |
| 8,517,726 B2 | 8/2013 | Kakavand et al. |
| 8,562,337 B2 | 10/2013 | Kuo et al. |
| 8,636,513 B2 | 1/2014 | Wen |
| 8,641,414 B2 | 2/2014 | Borovinskih et al. |
| 8,684,729 B2 | 4/2014 | Wen |
| 8,689,795 B2 | 4/2014 | Lee et al. |
| 8,708,697 B2 | 4/2014 | Li et al. |
| 8,758,009 B2 | 6/2014 | Chen et al. |
| 8,765,031 B2 | 7/2014 | Li et al. |
| 8,771,149 B2 | 7/2014 | Rahman et al. |
| 8,776,391 B1 | 7/2014 | Kaza et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,108,338 B2 | 8/2015 | Sirovskiy et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,403,238 B2 | 8/2016 | Culp |
| 9,433,476 B2 | 9/2016 | Khardekar et al. |
| 9,610,141 B2 * | 4/2017 | Kopelman ............... A61C 7/08 |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 9,943,386 B2 | 4/2018 | Webber et al. |
| 9,943,991 B2 | 4/2018 | Tanugula et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,336,102 B2 | 7/2019 | Cole |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,495,973 B2 | 12/2019 | Cole |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,783,629 B2 | 9/2020 | Parpara et al. |
| 10,813,720 B2 | 10/2020 | Grove et al. |
| 10,820,967 B2 * | 11/2020 | Li ............... A61C 7/08 |
| 10,874,483 B2 * | 12/2020 | Boronkay ............... A61C 7/08 |
| 10,881,487 B2 | 1/2021 | Cam et al. |
| 10,888,395 B2 | 1/2021 | Kopelman |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 * | 6/2021 | Kuo ............... A61C 7/08 |
| 11,045,282 B2 | 6/2021 | Kopelman et al. |
| 11,045,283 B2 | 6/2021 | Riley et al. |
| 11,103,330 B2 | 8/2021 | Webber et al. |

(56) References Cited

U.S. PATENT DOCUMENTS

| | | |
|---|---|---|
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,189,021 B2 | 11/2021 | Shah et al. |
| 11,219,506 B2 | 1/2022 | Shanjani et al. |
| 11,259,896 B2 | 3/2022 | Matov et al. |
| 11,273,011 B2 * | 3/2022 | Shanjani ............... B33Y 80/00 |
| 11,278,375 B2 | 3/2022 | Wang et al. |
| 11,295,444 B2 | 4/2022 | Cherkas et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2004/0243361 A1 | 12/2004 | Steuben et al. |
| 2005/0014105 A1 | 1/2005 | Abolfathi et al. |
| 2005/0129901 A1 | 6/2005 | Swindler et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0093982 A1 | 5/2006 | Wen |
| 2006/0093987 A1 | 5/2006 | Wen |
| 2006/0093993 A1 | 5/2006 | Wen |
| 2006/0115782 A1 | 6/2006 | Li et al. |
| 2006/0115785 A1 | 6/2006 | Li et al. |
| 2006/0127850 A1 | 6/2006 | Wen |
| 2006/0127857 A1 | 6/2006 | Zhenhuan et al. |
| 2006/0127858 A1 | 6/2006 | Wen |
| 2006/0127859 A1 | 6/2006 | Wen |
| 2006/0127860 A1 | 6/2006 | Wen |
| 2006/0172250 A1 | 8/2006 | Wen |
| 2006/0199142 A1 | 9/2006 | Liu et al. |
| 2006/0199145 A1 | 9/2006 | Liu et al. |
| 2006/0234179 A1 | 10/2006 | Wen et al. |
| 2007/0092853 A1 | 4/2007 | Liu et al. |
| 2007/0243502 A1 | 10/2007 | Wen |
| 2008/0022342 A1 | 1/2008 | Inatomi et al. |
| 2008/0083348 A1 | 4/2008 | Kuo et al. |
| 2008/0118882 A1 | 5/2008 | Su |
| 2008/0160473 A1 | 7/2008 | Li et al. |
| 2008/0224342 A1 | 9/2008 | Dowd |
| 2008/0248443 A1 | 10/2008 | Chishti et al. |
| 2008/0254402 A1 | 10/2008 | Hilliard |
| 2008/0286716 A1 | 11/2008 | Sherwood |
| 2008/0286717 A1 | 11/2008 | Sherwood |
| 2009/0148814 A1 | 6/2009 | Li et al. |
| 2009/0280450 A1 | 11/2009 | Kuo |
| 2010/0055635 A1 | 3/2010 | Kakavand |
| 2010/0129763 A1 | 5/2010 | Kuo |
| 2011/0079936 A1 | 4/2011 | Oxman |
| 2011/0269092 A1 | 11/2011 | Kuo et al. |
| 2013/0095446 A1 * | 4/2013 | Andreiko ............... A61C 7/002 |
| | | 128/848 |
| 2014/0067334 A1 | 3/2014 | Kuo |
| 2015/0064641 A1 * | 3/2015 | Gardner ................. A61C 9/004 |
| | | 700/98 |
| 2015/0265376 A1 | 9/2015 | Kopelman |
| 2015/0366638 A1 | 12/2015 | Kopelman et al. |
| 2016/0081769 A1 * | 3/2016 | Kimura .................. A61C 7/002 |
| | | 433/7 |
| 2016/0193014 A1 | 7/2016 | Morton et al. |
| 2016/0238251 A1 * | 8/2016 | Chang ..................... F23R 3/002 |
| 2016/0242871 A1 | 8/2016 | Morton et al. |
| 2017/0007360 A1 | 1/2017 | Kopelman et al. |
| 2017/0007361 A1 | 1/2017 | Boronkay et al. |
| 2017/0007363 A1 * | 1/2017 | Boronkay ............ A61C 1/0046 |
| 2017/0007366 A1 | 1/2017 | Kopelman et al. |
| 2017/0007386 A1 | 1/2017 | Mason et al. |
| 2017/0037867 A1 | 2/2017 | Moricca |
| 2017/0065373 A1 * | 3/2017 | Martz ..................... A61C 7/002 |
| 2017/0135792 A1 | 5/2017 | Webber |
| 2017/0135793 A1 | 5/2017 | Webber et al. |
| 2017/0165032 A1 | 6/2017 | Webber et al. |
| 2017/0360534 A1 * | 12/2017 | Sun ......................... B33Y 70/10 |
| 2018/0021107 A1 | 1/2018 | Benarouch et al. |
| 2018/0078343 A1 | 3/2018 | Falkel |
| 2018/0110591 A1 * | 4/2018 | Sato ........................ B29C 53/36 |
| 2018/0132975 A1 | 5/2018 | Wu et al. |
| 2018/0264719 A1 * | 9/2018 | Rolland .................. G03F 7/027 |
| 2018/0338819 A1 | 11/2018 | Chou |
| 2018/0353264 A1 * | 12/2018 | Riley .................... A61C 8/0096 |
| 2018/0360567 A1 | 12/2018 | Xue et al. |
| 2018/0368944 A1 * | 12/2018 | Sato ........................... A61C 7/10 |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0029775 A1 | 1/2019 | Morton et al. |
| 2019/0033719 A1 * | 1/2019 | Cole ....................... C08F 218/04 |
| 2019/0046297 A1 | 2/2019 | Kopelman et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0160734 A1 * | 5/2019 | Biesboer ................... C08L 23/06 |
| 2019/0175304 A1 | 6/2019 | Morton et al. |
| 2019/0262101 A1 * | 8/2019 | Shanjani ................... A61C 7/08 |
| 2019/0298494 A1 | 10/2019 | Webber et al. |
| 2019/0314119 A1 | 10/2019 | Kopelman et al. |
| 2019/0343606 A1 | 11/2019 | Wu et al. |
| 2019/0377327 A1 | 12/2019 | Griffin, III et al. |
| 2019/0388189 A1 | 12/2019 | Shivapuja et al. |
| 2020/0000553 A1 | 1/2020 | Makarenkova et al. |
| 2020/0061920 A1 * | 2/2020 | Debora .................. B29C 64/336 |
| 2020/0078137 A1 | 3/2020 | Chen et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0130237 A1 | 4/2020 | Mojdeh et al. |
| 2020/0140614 A1 | 5/2020 | Parkar et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0253696 A1 | 8/2020 | Raby et al. |
| 2020/0290262 A1 | 9/2020 | Aguilar Mendez et al. |
| 2020/0306017 A1 | 10/2020 | Chavez et al. |
| 2020/0316856 A1 | 10/2020 | Mojdeh et al. |
| 2020/0390523 A1 | 12/2020 | Sato et al. |
| 2020/0397537 A1 | 12/2020 | Raby et al. |
| 2021/0030516 A1 | 2/2021 | O'Leary et al. |
| 2021/0078357 A1 | 3/2021 | Venkatasanthanam et al. |
| 2021/0147672 A1 | 5/2021 | Cole et al. |
| 2021/0169617 A1 | 6/2021 | Nishimuta et al. |
| 2021/0220087 A1 | 7/2021 | Kopelman et al. |
| 2021/0317297 A1 | 10/2021 | Jena et al. |
| 2022/0031426 A1 | 2/2022 | Sato et al. |
| 2022/0110719 A1 * | 4/2022 | Chavez ..................... B33Y 70/10 |
| 2022/0162362 A1 | 5/2022 | Dorfinger et al. |

* cited by examiner

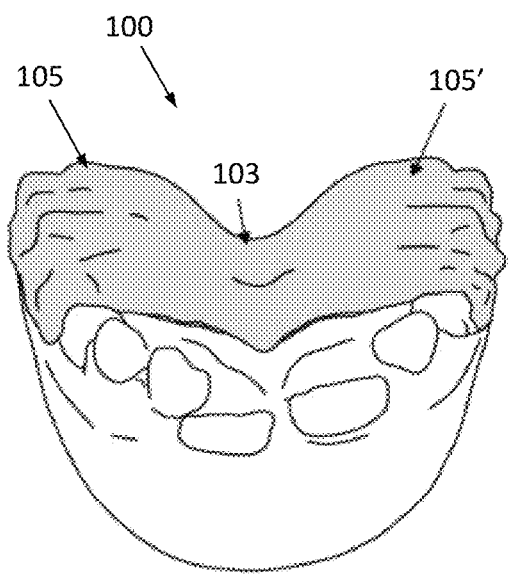
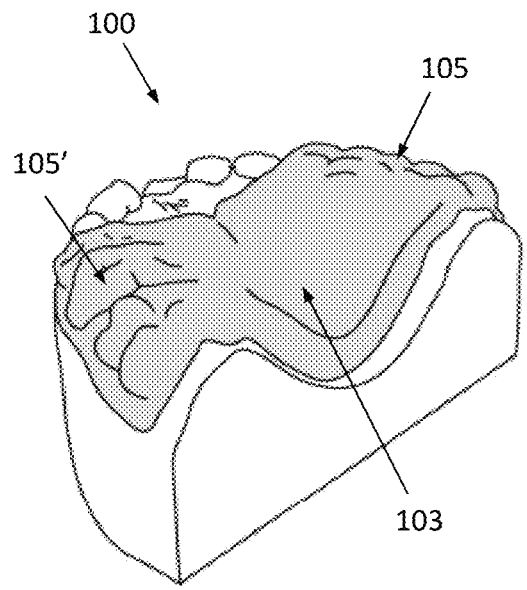
FIG. 1A  FIG. 1B
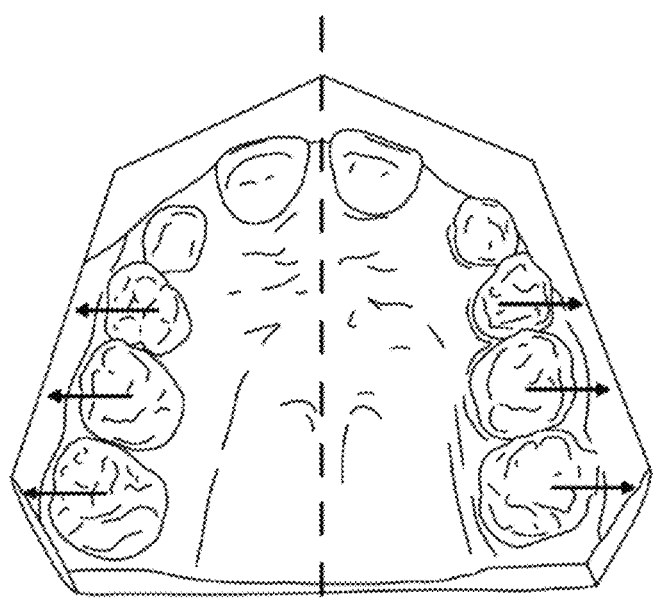
FIG. 1C

ACTIVE EXPANDERS

PASSIVE HOLDER (RETAINER)

MODULAR FABRICATION OF DENTAL APPARATUSES

CLAIM OF PRIORITY

This patent application claims priority to U.S. Provisional Patent Application No. 63/090,092, titled "MULTIPLE MATERIAL PALATAL EXPANDERS AND TECHNIQUES FOR MAKING THE SAME," and filed on Oct. 9, 2020, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The technical field relates to dental appliances, such as palatal expanders, aligners, and dental attachment templates, and to the various methods for making and using these dental appliances.

BACKGROUND

Dental devices, such as palatal expanders, dental aligners and attachment formation templates, are used to perform particular functions in accordance with respective treatment plans. For example, incremental palatal expanders can include a set of dental appliances that fit into a palate of a patient and function to expand a patient's palate according to a treatment plan. Aligners can include polymeric dental appliances that include tooth-receiving cavities to receive and reposition a patient's teeth to correct malocclusions. Dental attachment templates can include dental appliances shaped to fit to a patient's dentition and allow for the placement of attachments, e.g., bonded attachments, prefabricated attachments, etc. to the patient's dentition.

It is often desirable for dental appliances to be easy to use (e.g., easy to insert/remove), comfortable, and effective in administering treatment. As an example, it may be desirable for some regions of a dental appliance to be more rigid than other more compliant regions of the dental appliance.

SUMMARY

Described herein are dental devices and methods of making and using them. For example, described herein are palatal expanders with relatively rigid structures for exerting an expansion force for expanding the palate and relatively flexible structures that aid in the insertion and removal within the oral cavity.

The dental devices and methods described herein address the problem of fabricating dental appliances, such as incremental palatal expanders (and aligners with mandibular advancement features and attachment formation templates) where it is desirable to have competing properties. The methods may involve using multiple polymer materials in different regions of a dental appliance.

Different materials can be chosen based on physical properties for accomplishing different functions. For example, incremental palatal expanders, aligners (e.g., aligners with or without mandibular advancement structures and/or other structures), dental attachment templates, and/or other dental appliances made according to the techniques described herein can include different regions with different stiffnesses. In the case of incremental palatal expanders, for instance, a dental appliance may include a palatal region having a first stiffness that provides necessary forces to expand the patient's palate and tooth engagement region(s) that contact and engage with the patient's teeth to support the palatal region. The tooth engagement region(s) may be less stiff than the palatal region and may be relatively compliant (compared to the palatal region) for easy insertion and removal from the oral cavity.

For an example of a dental appliance (e.g., an aligner) with mandibular advancement structures, mandibular advancement structures on a dental appliance may include a first region (or regions) that are stiff enough to exert forces on a patient's mandible to move the patient's mandible toward a corrected position for, e.g., orthodontic treatment, correction of obstructive sleep apnea (OSA), etc. A dental appliance with mandibular advancement structures may also include a second region or regions that are less stiff than the first regions; the second region(s) may perform other functions and may be relatively compliant compared to the first regions. The second regions of a dental appliance with mandibular advancement structures may facilitate, e.g., insertion and/or removal, may include tooth-receiving cavities that are configured to move a patient's teeth in order to correct malocclusions, align the patient's teeth, etc.

For yet another example relating to attachment formation templates (e.g., appliances used to place attachments that engage with attachment wells and/or other structures in aligners to exert repositioning forces on a patient's dentition) may include first regions that comprise pre-fabricated (e.g., 3D printed) attachments that break off the attachment template to be bonded on a patient's teeth; these appliances may include second regions used to, e.g., engage the patient's teeth, locate the pre-fabricated attachments on the parts of the patient's dentition where the pre-fabricated attachments can be broken off from the dental attachment template and bonded to the patient's teeth, etc. For attachment formation templates, it may be desirable for regions corresponding to pre-fabricated attachment regions to have a stiffness that approximates or exceeds the stiffness of a bonded attachment. It may be further desirable for support regions to be relatively compliant/less-stiff (than the pre-fabricated attachment regions) so the support regions can be inserted into/removed from a patient's teeth and/or place pre-fabricated attachment regions appropriately. As a result, for many attachment formation templates, it may be desirable for support regions that engage with teeth and/or position attachments to have different properties than the pre-fabricated attachment regions corresponding to pre-fabricated dental attachments.

Various methods may be used to form dental devices. In some embodiments, separate parts of a dental appliance are formed and then coupled together to form the dental appliance. For instance, separate parts may be formed independently and made from different materials, then pieced together to make a single multi-material dental appliance. In various embodiments, different materials can be coupled to form a single dental appliance via adhesion (e.g., with or without accompanying design features), mechanically (e.g., with or without inter-locking mechanical features), and/or using one or more fasteners.

In some embodiments, two or more materials are used as part of a photopolymer-based additive manufacturing method to form a first part with a first set of properties (rigidity, expansion-force-exerting properties, etc.) out of a first material, form a second part with a second set of properties (rigidity, expansion-force-exerting properties, etc.) out of a second material, optionally form interface areas (referred to as transition regions) between the first and second portions, and optionally form other portions as needed. An example of a process to make a dental appliance from two or more materials involves using an inkjet printing process. In some cases, this could occur as part of a single additive manufacturing process where different materials are added to a vat and used to additive manufacture different parts from different materials, interfaces, and/or other regions. In some embodiments, this could occur as part of a scalable industrial manufacturing process that is used for volume production of dental appliances for patients.

Any of the techniques described herein can be applied toward fabrication of any of a number of dental devices, such as to incremental palatal expanders, aligners, dental appliances with mandibular advancement portions, attachment formation templates, etc. Incremental palatal expanders formed according to the techniques described herein may include a tooth engagement region for engaging at least a portion of the teeth in the patient's upper jaw, e.g., the molars, and a palatal region extending between the tooth engaging region that is configured to be positioned adjacent and opposite from the patient's palate when the device is worn by the patient. For example, an incremental palatal expander may include a pair of tooth engagement regions on either side of the device and connected by a palatal region. The tooth engagement regions of any of the incremental palatal expanders described herein may include one or more removal features to allow the patient to remove the apparatus once attached to the patient's dentition. As noted herein, the removal features may be more compliant (e.g., less stiff) than the palatal regions so that the dental appliance can be inserted into/removed from a patient's mouth conveniently. In some implementations, the palatal region of the palatal expander provides a force ranging from about 8 N and 120 N against either side of the upper palate and/or lingual side of the teeth. In various implementations, an incremental palatal expander can be one of a series of incremental palatal expanders used to expand a patient's palate from an initial size/configuration toward a target size/configuration. A series of incremental palatal expanders (IPEs) may be sequentially worn over time to expand a subject's palate as part of a treatment plan. All or some of these IPEs may be fabricated as described herein. Each IPE may be worn for a predetermined time period, such as one day, two days, three days, etc. and then removed (including removed by the patient or parent/guardian) and replaced with next IPE in the series.

According to some aspects, an incremental palatal expander includes: a palatal region shaped to fit in a patient's upper jaw and apply a translational force across a patient's palate, wherein the palatal region is made of a first polymer material having a rigidity sufficient to apply a translation force in accordance with a palatal expansion treatment plan; a tooth engagement region having one or more cavities shaped to accommodate one or more corresponding teeth, wherein the tooth engagement region is made of a second polymer material that is less rigid than the first polymer material; and a junction coupling the tooth engagement region and the palatal region. One or both of the first and second materials may be composite materials that include fillers, fibers, and the like. The junction can include an adhesive to bond the palatal region with the tooth engagement region. The adhesive may chemically bond the palatal region with the tooth engagement region. One or both of the palatal region and the tooth engagement region may include a textured joining surface that enhances the bond between the palatal region and the tooth engagement region. One or both of the palatal region and the tooth engagement region may include a joining mechanism that mechanically couples the tooth engagement region and the palatal region, the joining mechanism include one or more of a spring-type fastener, a press-fit fastening system, an interlocking system, a V-shaped press fit system, and a slotted feature system. The palatal expander can include two tooth engagement regions each coupled to opposing sides of the palatal region. The palatal expander can be adapted to provide a force ranging from about 8 N and 120 N against either side of the upper palate and/or lingual side of the teeth. In some implementations, the palatal region of the palatal expander provides a force ranging from about 8 N and 120 N against either side of the upper palate and/or lingual side of the teeth. In various implementations, an incremental palatal expander can be one of a series of incremental palatal expanders used to expand a patient's palate from an initial size/configuration toward a target size/configuration.

According to some aspects, a method of forming a palatal expander includes: forming a palatal region of the palatal expander using a first polymer material having a rigidity sufficient to apply the translation force in accordance with a palatal expansion treatment plan; forming tooth engagement regions using a second polymer material that is less rigid than the first polymer material, wherein the tooth engagement regions include one or more cavities shaped to accommodate one or more corresponding teeth; and forming the palatal expander by coupling the tooth engagement regions to opposing sides of the palatal region. The method may further include determining a relative shrinkage factor associated with the first and second polymer materials, and adjusting at least one three-dimensional model for forming the palatal region or the tooth engagement regions based on the shrinkage factor. The first polymer material may be a composite polymer material including fibers or metal material integrated therein. Coupling the tooth engagement regions to opposing sides of the palatal region includes applying an adhesive to joining surfaces of the palatal region and the tooth engagement regions. Forming the palatal region may include forming a texture on the joining surfaces of the palatal region and the tooth engagement regions, wherein the adhesive is applied on the textured joining surfaces.

According to some aspects, a dental device includes: a first region made of a first polymer material having a first rigidity; a second region made of a second polymer material having a second rigidity that is less than the first rigidity; and a transition region coupling the first region and the second region, the transition region including a mixture of the first polymer material and the second polymer material. In some cases, the transition region has a sharp transition between the first and second polymer materials. The first region may be shaped to fit in a patient's upper jaw and apply a translational force across a patient's palate. The second region may include one or more cavities shaped to accommodate one or more corresponding teeth. The mixture may be a homogenous mixture of the first and second polymer materials. The first polymer material may be a composite polymer material including fibers or metal material integrated therein. The transition region may include multiple portions each having different relative amounts of the first and second polymer materials. The multiple portions may provide a gradual gradient of material change within the transition region. The palatal expander can be adapted to provide a force ranging from about 8 N and 120 N against either side of the upper palate and/or lingual side of the teeth. In some implementations, the palatal region of the palatal expander provides a force ranging from about 8 N and 120 N against either side of the upper palate and/or lingual side of the teeth. In various implementations, an incremental palatal expander can be one of a series of incremental palatal expanders used to expand a patient's palate from an initial size/configuration toward a target size/configuration.

According to some aspects, a method of forming a dental device includes: forming a first region of the dental device using a first polymer material having a first rigidity; forming a second region of the dental device using a second polymer material having a second rigidity that is less than the first rigidity; and forming a transition region coupling the first region and the second region, the transition region including a homogenous mixture of the first polymer material and the second polymer material. Forming the transition region may include forming a liquid of a mixture of monomer/oligomer forms of the first and second polymer materials and incrementally curing the liquid. The liquid may be cured using any of a number of techniques. For example, the liquid may be cured layer by layer (e.g., using one or more beams of electromagnetic radiation) and/or using a light projection process Forming the transition region may include forming multiple portions of the transition region having different relative amounts of the first and second polymer materials. Forming the multiple portions may include changing a first material to second material ratio such that each portion has a different first material to second material ratio. Examples of dental devices that may be created according to these implementations include: incremental palatal expanders, attachment formation templates, dental appliances with mandibular advancement features, etc.

According to some aspects, a method of forming a dental device includes: forming a first region of the dental device using a first polymer material having a first rigidity; forming a second region of the dental device using a second polymer material having a second rigidity that is less than the first rigidity; and forming a transition region coupling the first region and the second region, the transition region including a homogenous mixture of the first polymer material and the second polymer material. Forming the transition region may include forming a liquid of a mixture of monomer/oligomer forms of the first and second polymer materials and incrementally curing the liquid layer by layer using a laser beam. Forming the transition region may include forming multiple portions of the transition region having different relative amounts of the first and second polymer materials. Forming the multiple portions may include changing a first material to second material ratio such that each portion has a different first material to second material ratio. Examples of dental devices that may be created according to these implementations include: incremental palatal expanders, attachment formation templates, dental appliances with mandibular advancement features, etc.

Any of these methods described herein may include forming the junction region (the junction) between the different materials of the palatal region and the tooth engagement region so that the forces applied by the palatal region and/or the tooth engagement region are distributed to the patient and/or across the device in a desired manner. In general the forces applied by the palatal expander may be lower than those applied by traditional palatal expanders, but may be distributed across a larger engagement region and may therefore be somewhat lower. The forces applied may be more constant and/or consistent. Thus, any of these methods and apparatuses for making them may be configured to determine the location and shape of the junction region. In some examples, described herein are apparatuses for forming a palatal expander having a palatal region and a tooth engagement region formed of different materials, as well as a junction region coupling the tooth engagement region and the palatal region, in which the apparatus includes a junction planning module that identifies the location and/or shape of the junction region so as to distribute the forces applied by the palatal region uniformly distributed at target application sites. The apparatus may include software, hardware and/or firmware. For example, the apparatus may be or may include a non-transitory computer-readable storage medium storing a set of instructions capable of being executed by a processor (e.g., computer, tablet, smartphone, etc.). In some examples, the apparatuses or methods described herein may define the junction region based on the material properties of the different materials forming the palatal region and the tooth engagement region, as well as the patient's dentition and may be configured to distribute the force(s) applied, e.g., transverse forces applied to expand the palate, so that the forces are constant.

As mentioned, also described herein are apparatuses (including systems, and software) for performing the methods described herein. For example, described herein are non-transitory computer-readable storage medium storing a set of instructions capable of being executed by a processor, that when executed by the processor causes the processor to perform the method of: forming a digital model of a palatal expander including a palatal region and a tooth engagement region; setting the material of the palatal region to a first polymer material having a rigidity sufficient to apply a translation force to expand a patient's palate in accordance with a palatal expansion treatment plan; setting the material of the tooth engagement regions to a second polymer material that is less rigid than the first polymer material, wherein the tooth engagement region includes one or more cavities shaped to accommodate one or more corresponding teeth; and outputting instructions for forming the palatal expander in which the tooth engagement region is joined to the palatal region at a junction.

The medium may also include instructions for determining a relative shrinkage factor associated with the first and second polymer materials, and adjusting one or both of the palatal region or the tooth engagement regions of the digital model of the palatal expander based on the shrinkage factor. In some examples setting the first polymer material comprises setting the first polymer material to a composite polymer material including fibers or metal material integrated therein.

The medium may also include instructions for determining the junction so that the translation force is distributed over a region of the tooth engagement region.

The medium may also include instructions for setting a texture on the joining surfaces of the palatal region and the tooth engagement regions, so that an adhesive may be applied on the textured joining surfaces.

In general, the medium may also include instructions for forming the palatal expander from the instructions by an additive manufacturing technique.

For example, also described herein are non-transitory computer-readable storage medium storing a set of instructions capable of being executed by a processor, that when executed by the processor causes the processor to perform the method of: forming digital model of a palatal expander including a first region and a second region; setting a first polymer material having a first rigidity for the first region of the dental device; setting a second polymer material having a second rigidity that is less than the first rigidity for the second region of the dental device; specifying a transition region between the first region and the second region, the transition region including a homogenous mixture of the first polymer material and the second polymer material; and outputting instructions for forming the palatal expander using the digital model.

Specifying the transition region may comprise determining a size and shape of the transition region to distribute lateral forces from the first region when the first region is worn over a patient's palate and the second region is worn over the patient's teeth. In some examples specifying the transition region comprises specifying multiple portions of the transition region having different relative amounts of the first and second polymer materials. Specifying the multiple portions may include identifying a ratio of the first polymer material to the second polymer material such that differ portions of the multiple portions have a different first material to second material ratio.

As mentioned above, the medium may also include instructions for forming the palatal expander from the instructions by an additive manufacturing technique.

Examples of dental appliances, including palatal expanders, having features that may be used with any of the features and methods described herein may be found, for example, in U.S. Patent Application Publication No. 2018/0153648A1, filed on Dec. 4, 2017, and entitled "PALATAL EXPANDERS AND METHODS OF EXPANDING A PALATE," which is incorporated herein by reference in its entirety.

For example, described herein are three-dimensionally (3D) printed dental devices comprising: a first 3D printed region is made of a first polymer resin material having a first rigidity; a second 3D printed region made of a second polymer resin material that is less rigid than the first polymer material; and a junction coupling the first region and the second region.

The dental device may be selected from the group consisting of: a palatal expander, an attachment template, an aligner including a mandibular repositioning block, and a variable property aligner. The first region may be configured to fit in a patient's upper jaw and apply a translational force across a patient's palate, as described above.

The junction may include an adhesive to bond the first region with the second region. The adhesive may chemically bond the first region with the second region. One or both of the first region and the second region may include a textured joining surface that enhances the bond between the first region with the second region. One or both of the first region and the second region may include a joining mechanism that mechanically couples the second region and the first region, the joining mechanism may include one or more of a spring-type fastener, a press-fit fastening system, an interlocking system, a V-shaped press fit system, and a slotted feature system.

Also described herein are methods of forming a three-dimensionally (3D) printed dental device, the method comprising: forming a first 3D printed region using a first polymer resin material having a first rigidity; forming a second 3D printed region using a second polymer resin material that is less rigid than the first polymer resin material; and forming the dental device by coupling the first region to second region.

As mentioned, the dental device may be selected from the group consisting of: a palatal expander, an attachment template, an aligner including a mandibular repositioning block, and a variable property aligner. Any of these methods may include determining a relative shrinkage factor associated with the first and second polymer resin materials, and adjusting at least one 3D model for forming the first region or the second region based on the relative shrinkage factor.

The first polymer resin material may be a composite polymer material including fibers or metal material integrated therein. Coupling the first region to the second region may include applying an adhesive to joining surfaces of the first region and the second region.

Forming the first region may include forming a texture on the joining surfaces of the first region and the second region, wherein the adhesive is applied on the textured joining surfaces.

Also described herein are non-transitory computer-readable storage medium storing a set of instructions capable of being executed by a processor, that when executed by the processor causes the processor to perform a method of: forming a digital model of a dental device including a first region and a second region; setting a material of the first region to a first polymer resin material having a first rigidity in accordance with a treatment plan; setting a material of the second regions to a second polymer resin material that is less rigid than the first polymer resin material; and outputting instructions for forming the dental device in which the second region is joined to the first region at a junction.

These and other aspects are described herein.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

FIGS. 1A and 1B illustrate an example of a palatal expander. FIG. 1A is a front perspective view of a bottom side (tongue-facing side) of the palatal expander, shown attached on a model of a patient's upper dental arch. FIG. 1B is a back-perspective view of the palatal expander of FIG. 1A.

FIG. 1C illustrates translational forces that may be applied by a palatal expander to a patient's palate (arrows) to expand the palate, for example, braking and separating the palatal midline suture.

FIG. 4A illustrates an example of a tooth engagement region. FIG. 4B illustrates an example of a palatal region 402.

FIG. 18A shows a side view of an upper jaw with a first mandibular repositioning jaw element and a lower jaw with a repositioning jaw element. FIG. 18B illustrates a front view of an upper jaw with a first repositioning jaw element and a third repositioning jaw element and a lower jaw with a second repositioning jaw element and a fourth repositioning jaw element. FIG. 18C illustrates a side view of a first aligner shell with a first repositioning jaw element (mandibular repositioning block) and a second shell with a second repositioning jaw element (mandibular repositioning block).

FIG. 19A is a side view of an upper jaw with a first repositioning jaw element (mandibular repositioning block) and a lower jaw with a second repositioning jaw element (mandibular repositioning block). FIG. 2B shows a front view of an upper jaw with a first repositioning jaw element (mandibular repositioning block) and a third repositioning jaw element (mandibular repositioning block) and a lower jaw with a second repositioning jaw element (mandibular repositioning block) and a fourth repositioning jaw element (mandibular repositioning block).

DETAILED DESCRIPTION

Figure 2:
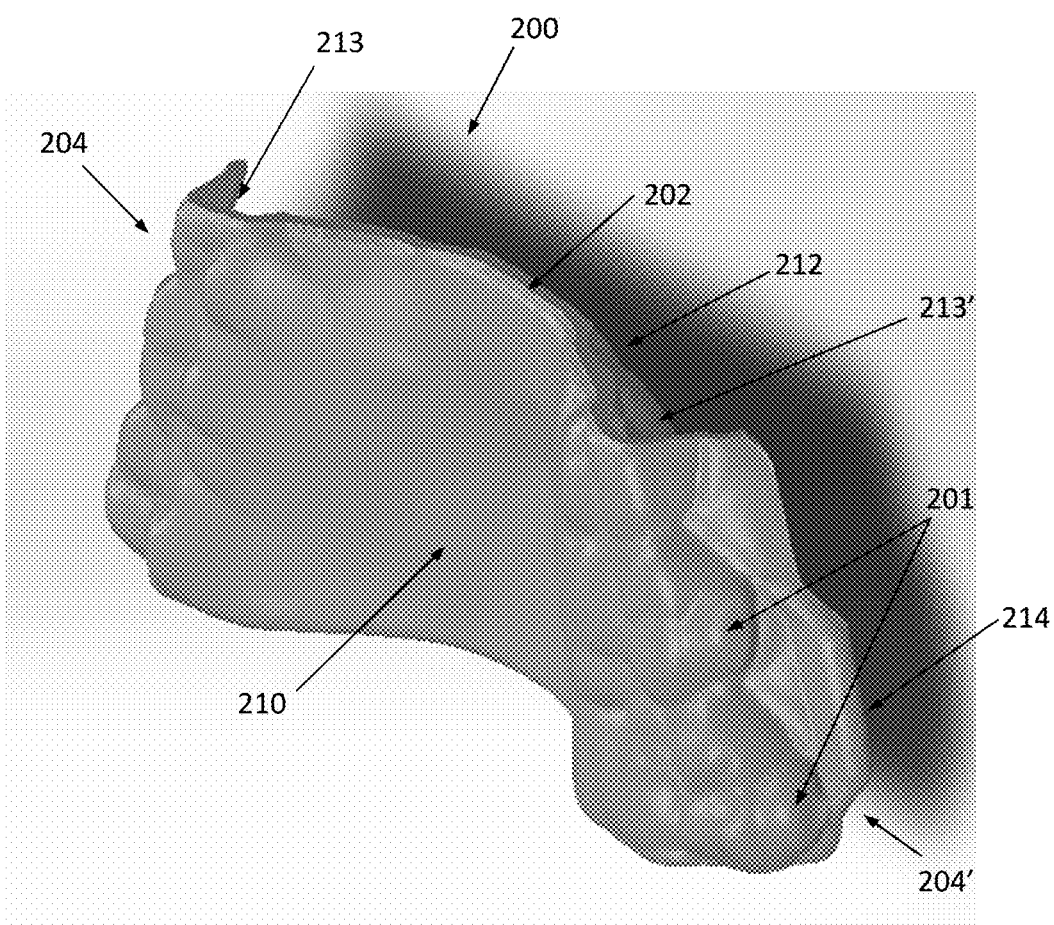
FIG. 2 illustrates a perspective view of an example palatal expander.

In general, the dental devices described herein are worn on a patient's teeth and are used in accordance with a treatment plan for treating a patient's dental needs. The methods described herein can be used to form a single dental device made of multiple materials arranged in different regions of the device to optimize performance and comfort. In some cases, a series of dental devices are formed using the methods describe herein, where each dental device is configured to achieve a particular goal as part of the treatment plan. It should be noted that the devices and methods described herein are not limited any particular type of dental device. Non-limiting examples of dental devices can include palatal expanders, palatal dental aligners (e.g., having mandibular advancement blocks) and/or attachment formation template devices.

All or portions of dental devices described herein may fabricated using any fabrication techniques, such as any of a number of additive manufacturing (e.g., 3D printing, binder jetting, etc.) techniques and/or molding techniques. In some embodiments all or portions of the dental devices are formed using an injection molding process whereby one or more thermosetting polymer materials, while in molten form, is injected into a mold. In some cases, light and/or heat is used to cure the resin. Once hardened, the device may be removed from the mold, trimmed, cleaned and polished. In some cases, all or portions of the dental devices are formed using additive manufacturing technology where layers are sequentially added on top of each other based on one or more three-dimensional computer models of a target device. Other fabrication techniques for forming all or portions of a dental devices may include thermal dispensing ("thermo-doodle") methods, blow-molding, extrusion, pressure forming, casting and/or other manufacturing methods.

FIGS. 1A and 1B illustrate an example of a palatal expander 100, shown from different perspectives. These or similar palatal expanders may include any of the features described herein, separately or collectively. In this example, the palatal expander 100 is configured as a removable, e.g., patient-removable (with or without the use of a removing tool) that may be formed of one or more materials, including, e.g., a biocompatible polymer material(s). In some cases, the polymers may include a mixture or combination of photocurable resins that includes oligomers and monomers. In some cases, the polymers may include a mixture or combination of hydrophobic, hydrophilic and/or amphiphilic components including telechelic radical, ionic, urethane and/or cyanide ester oligomers, including but not limited to methacrylates and/or acrylates, epoxies, thiols, oxetanyls with at least one linkage of urethane, carbonates, sulfones, siloxanes, thiols, amides, amines, esters, ethers saturated and/or unsaturated alkyl chains (e.g., all either aromatic, cyclic, or linear), while also being biocompatible. Examples of monomer precursors may include vinyl esters, vinyl ethers, methacrylate/acrylates, thiols, epoxies, oxetanyls, or any combination thereof, while being biocompatible. The polymers may also have fillers such as inorganic and organic particles, fibers, nanotubes and/or thermoplastics ranging from 0.1 micrometers (μm) to 200 μm in various shapes that can be reactive or non-reactive.

In some examples, some or all of the palatal expander 100 is formed using additive manufacturing (e.g., 3D printing) and/or molding processes. A series of palatal expanders may be used and incrementally staged to expand a patient's palate. In some cases, the palatal expanders may be configured for treatment of children and young adults. The palatal expander 100 includes a tooth engagement region 105 for engaging at least a portion of the teeth in the patient's upper jaw, in particular the molars, and a palatal region 103 extending between the tooth engaging regions 105 and 105' and that is configured to be positioned adjacent the patient's palate when the device is worn by the patient. A surface of the palatal region 103 adjacent to the patent's palate may have a geometry adapted to fit against the shape of the patient's palate.

FIGS. 1A and 1B illustrate an example of a palatal expander 100, shown from different perspectives. These or similar palatal expanders may include any of the features described herein, separately or collectively. In this example, the palatal expander 100 is configured as a removable, e.g., patient-removable (with or without the use of a removing tool) that may be formed of one or more materials, including, e.g., a biocompatible polymer material(s). In some examples, some or all of the palatal expander 100 is formed using additive manufacturing (e.g., 3D printing or binder jetting) and/or molding processes. A series of palatal expanders may be used and incrementally staged to expand a patient's palate. In some cases, the palatal expanders may be configured for treatment of children and young adults. The palatal expander 100 includes a tooth engagement region 105 for engaging at least a portion of the teeth in the patient's upper jaw, in particular the molars, and a palatal region 103 extending between the tooth engaging regions 105 and 105' and that is configured to be positioned adjacent the patient's palate when the device is worn by the patient. A surface of the palatal region 103 adjacent to the patent's palate may have a geometry adapted to fit against the shape of the patient's palate.

The palatal region 103 may provide force to stretch or expand the palate (e.g., including the palatal midline suture). The palatal region 103 may be configured balance the load deflection for patient comfort. In some cases, the palatal region 103 may be configured to apply transverse forces distributed across teeth on either side of palate. For example, the forces may be distributed among three posterior teeth on each side, as shown in FIG. 1C, and or on a lateral side of the palate. The forces may be applied to the lingual side of the teeth (e.g., molars) and/or to the lateral side of the palate. In some cases, the palatal region 103 may include energy-enhancing features (e.g., springs and thermally active materials) and/or one or more adaptations, such as struts, supports, cross-beams, ribs, gaps/windows and/or attachments, which may distribute the forces applied in a more nuanced manner. For example, these devices may be configured so that the forces applied are distributed in a predetermined and/or desired pattern by arranging one or more points of contact between the palatal expander and the patient's mouth (e.g., in the gingiva and/or preferably along an upper or lower lateral portion of the patient's teeth, including their molars). The curvature (e.g., concavity) of the device may also be adjusted, to distribute the forces applied, while allowing clearance between the palate and the device, and/or allowing clearance for the user's tongue.

FIG. 2 shows another example of a palatal expander 200. A lingual side 210 of the device 200 can have a concave shape to allow space for the patient's tongue when wearing the device. All or a portion of a palatal side 212 of the device 200 may contact the patient's palate. The tooth engagement regions 204 and 204' can each include one or more cavities 213 and 213' for fitting on corresponding teeth of the patient. In some embodiments, the cavities 213 and 213' are shaped in accordance with the corresponding teeth to provide accurate registration of the palatal expander 200 when on the patient's dentition.

In the example of FIG. 2, the palatal expander 200 includes a removal feature 214 corresponding to an extension of the tooth engagement region 204' that is adapted to facilitate removal of the palatal expander 200 from the patient's teeth. For example, the removal feature 214 can be adapted to facilitate hooking of a finger (or fingernail) to provide leverage when removing the palatal expander 200 from the patient's palate. The removal feature 214 may be configured to extend toward or past the gingiva line when the palatal expander 200 is positioned on the patient's dentition. In some embodiments, the opposing engagement region 204 also includes a removal feature. Additionally or alternatively, the palatal expander may include one or more attachment features 201 on one or both sides of the device (e.g., in one or both of the tooth engagement regions 204 and 204'). The attachment features can correspond to cavities on one or both of the buccal sides of the tooth engagement regions 204 and 204', which are configured to couple with corresponding attachments bonded to the patient's teeth and to help retain the device 200 on the patient's teeth.

The dental devices described herein can include different regions that have different physical characteristics. For example, the tooth engagement regions 204 and 204' may have different properties than the palatal region 202. In some cases, the tooth engagement regions 204 and 204' may be made of a material(s) optimized for patient comfort while providing enough structural integrity to withstand occlusal forces. The material(s) of the tooth engagement regions 204 and 204' should have sufficiently high flexibility to bend while the patient fits the device on the teeth and removes the device from the teeth, thereby allowing for easier placement and removal of the palatal expander 200. The palatal region 202 may be made of a material(s) optimized for providing necessary forces across the palate to achieve a pre-determined extent of palate expansion. In some cases, the palatal region 202 is made of a first material and the tooth engagement regions 204 and 204' are made of a second material different than the first material.

The dental devices can be made of any of a number of materials or composite materials. In some cases, at least a portion of the palatal expander is made of a polymer material, such as a thermoset polymer and/or an elastomeric polymer. The polymer material(s) may be biocompatible and suitable for use in the patient's mouth. A composite material may include a polymer base material with a reinforcing material, such as a fibers (e.g., polymer fibers and/or natural fibers) and/or metal material, integrated therein. In some cases, the palatal region 202 is made of a first material, a first tooth engagement region 204 is made of a second material different than the first material, and a second tooth engagement region 204' is made of a third material different than the first and second materials. In some embodiments, the palatal region 202 are made of a more rigid material (e.g., polymer) than the material(s) of tooth engagement regions 204 and 204'. This can allow the palatal region 202 to be sufficiently rigid (stiffness) to provide the required expansion force while allowing the tooth engagement regions 204 and 204' to be flexible for optimal fitting on the patient's teeth and/or for patient comfort.

Figure 3A:
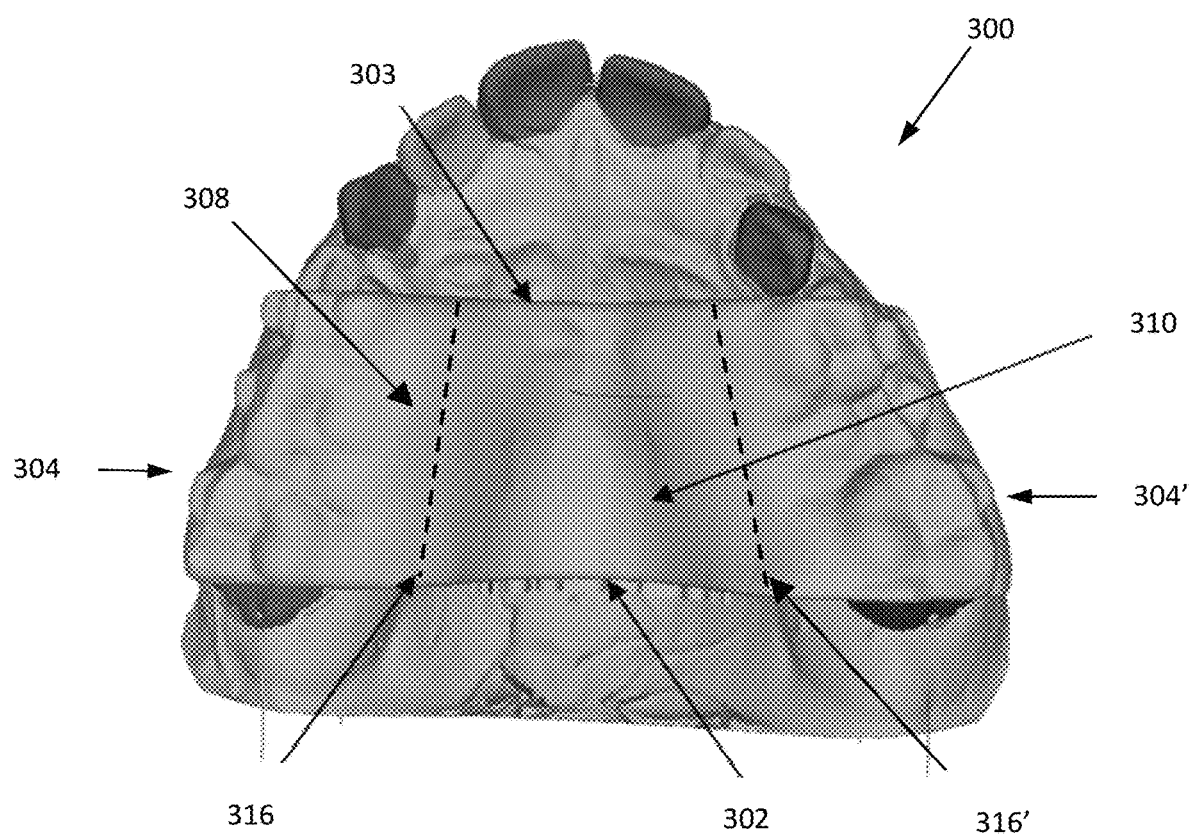
FIG. 3A illustrates a lingual view of an example palatal expander on an upper jaw, showing junctions between a palatal region and tooth engagement regions.

In some embodiments, the transition between the different regions of the palatal expander are defined by one or more junctions for joining the different regions. FIG. 3A shows a lingual side 310 of an example palatal expander 300 illustrating junctions 316 and 316' between the palatal region 302 (having an anterior portion 303) and the tooth engagement regions 304 and 304'. A first junction 316 corresponds to the region of the device 300 where a first tooth engagement regions 304 is connected to the palatal region 302. Likewise, a second junction 316' corresponds to the region of the device 300 where a second tooth engagement regions 304' is connected to the palatal region 302. In some examples, the first tooth engagement region 304, the palatal region 302 and the second tooth engagement region 304' are formed (e.g., printed) separately and then joined. The junction 316 shown in this example may be straight (e.g., shown by the dashed line) or it may be curved, including sinusoidal and/or non-straight. In some examples the junction (junction region) may be configured to distribute the forces (lateral forces) expanding the palate over regions of the tooth engagement region, and in particular over the lingual portion of the tooth engagement region 308 that may contact the gums or region more distal from the occlusal surface of the teeth. This may allow for smaller magnitude forces to be used while still achieving a significant palatal expansion.

The junctions 316 and 316' may include adhesive (e.g., epoxy), a weld (e.g., by molding), mechanical features (e.g., interference fit, locking features, etc.) and/or other type of connecting agents. The adhesive and/or weld may provide a chemical bond between the palatal region 302 and the tooth engagement regions 304 and 304'. The mechanical features may provide a physical connection between the palatal region 302 and the tooth engagement regions 304 and 304'. In some cases, the junctions 316 and 316' provide both chemical bonding and mechanical connection between the palatal region 302 and the tooth engagement regions 304 and 304'.

The modular design of the palatal expander 300 can allow the different regions (e.g., palatal region 302 and tooth engagement regions 304 and 304') to be fabricated separately, thereby allowing for greater manufacturing flexibility. For example, a palate expansion treatment typically involves providing a series of palatal expanders that progressive expand the patient's palate. Modular fabrication can allow for separate and customized modifications of the palatal region 302 and/or tooth engagement regions 304 and 304' when fabricating the series of palatal expanders. Once fabricated, the customized palatal region 302 can be coupled with customized tooth engagement regions 304 and 304'. In some instances, the tooth engagement regions 304/304' and the palatal region 302 are fixedly connected when the patient receives the device 300. In other instances, one or both of the tooth engagement regions 304/304' are separated from the palatal region 302 when the patient receives the device 300, and the patient is given instructions for connecting them.

Figure 3B:
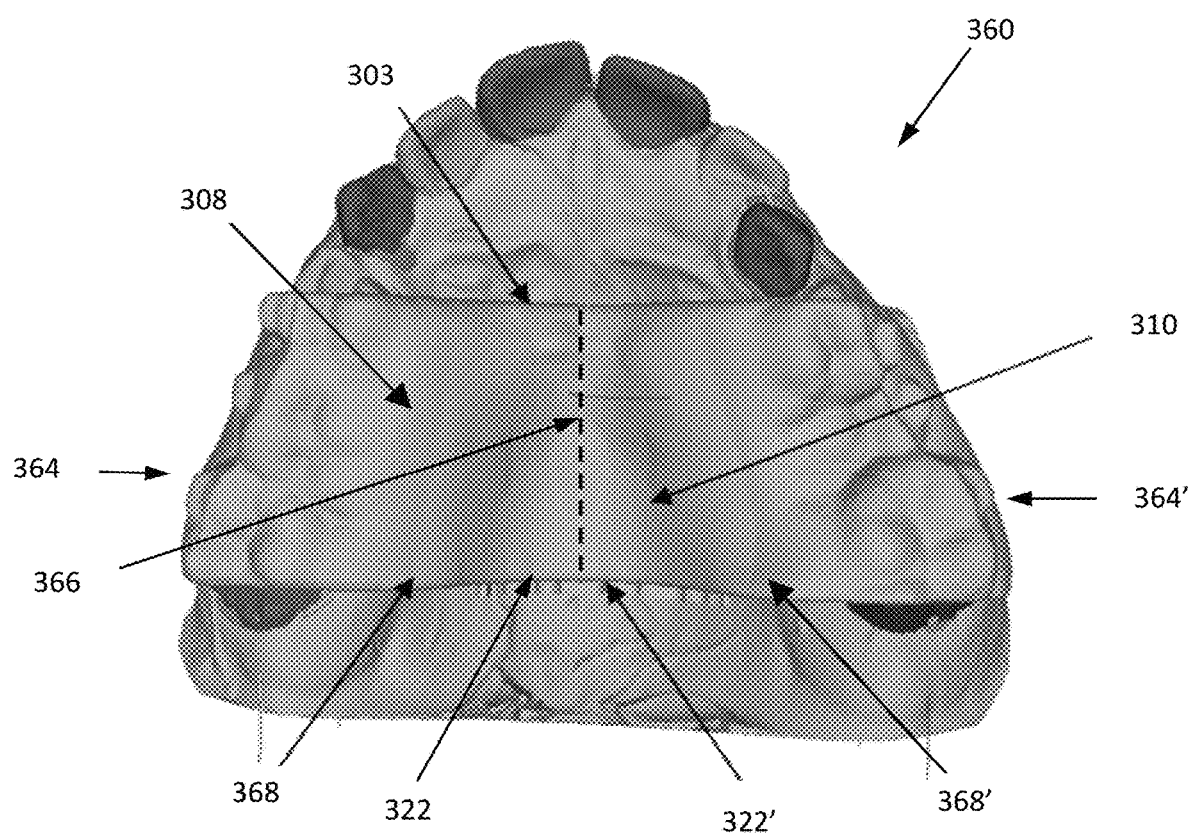
FIG. 3B illustrates a lingual view of another example palatal expander on an upper jaw having a single junction between two regions of the palatal expander.

The dental device may include any number of junctions that join separately formed regions. For example, referring to FIG. 3B, a palatal expander 360 can include a first region 368 and a second region 368' joined by a junction 366. The first region 368 can include a first tooth engagement portion 364 and first palatal portion 322. Likewise, the second region 368' can include a second tooth engagement portion 364' and second palatal portion 322'. The first region 368 and the second region 368' may be multi-material parts. For instance, the first and second palatal portions 322/322' may be made of a first material (e.g., more rigid material), and the first and second tooth engagement portions 364/364' may be made of a second material (e.g., less rigid material). The first and second materials may be integrally formed with each other using any of the techniques described herein such as the photopolymer-based and ink jetting additive techniques. After the first region 368 and the second region 368' are formed, they can be joined at the junction 366 using any of the techniques described herein (e.g., adhesive, weld and/or mechanical coupling). The junction(s) may be anywhere within the dental device. For example, the junction 366 may be in the middle of the palatal expander 360 or closer to one of the first tooth engagement portion 364 and the second tooth engagement portion 364'. The dental device can include any number of junctions, e.g., 1, 2, 3, 4, 5, 6, or more. The junction(s) may run lengthwise, crosswise and/or along any axis of the dental device.

Figure 4A:
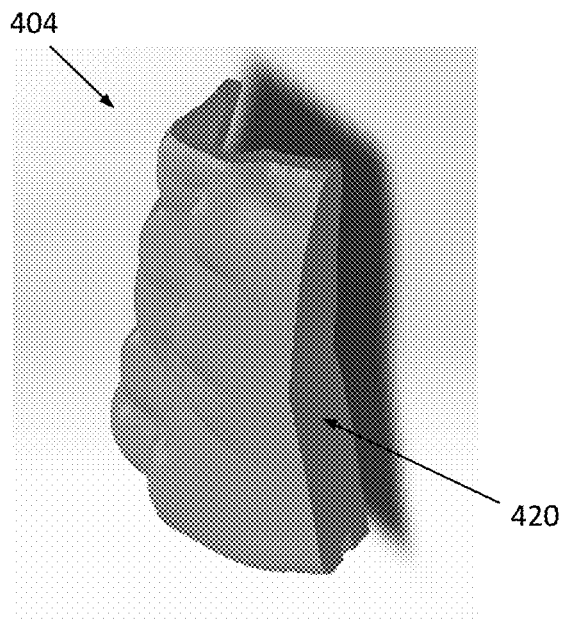
FIGS. 4A and 4B illustrate perspective views of separate regions of an example palatal expander.
Figure 4B:
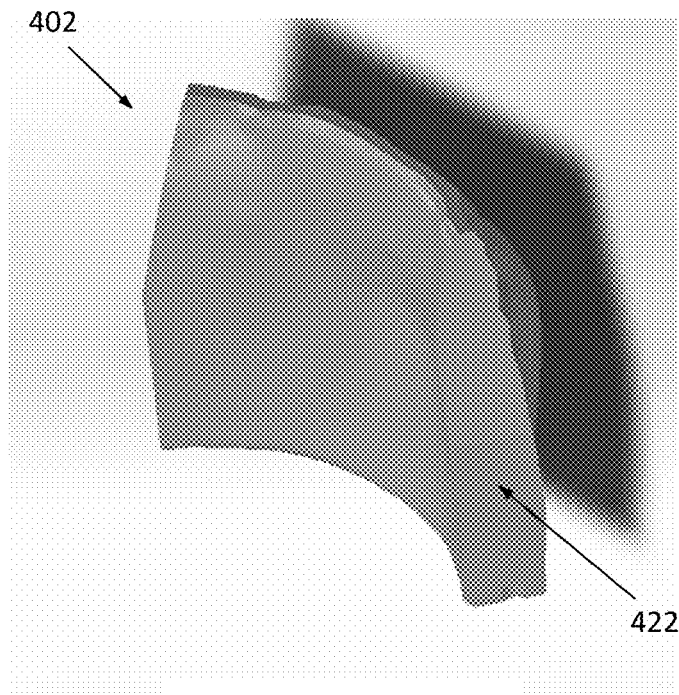

FIGS. 4A and 4B show examples of a tooth engagement region 404 and a palatal region 402, respectively. In this example, the tooth engagement region 404 includes an angled joining surface 420 configured to mate with a corresponding angled joining surface 422 of the palatal region 402. This angled joining surface configuration allows for a more robust junction between the regions once the regions are joined together (e.g., via adhesive, weld, and/or other type of connecting agent) compared to flat joining surface.

Figure 5:
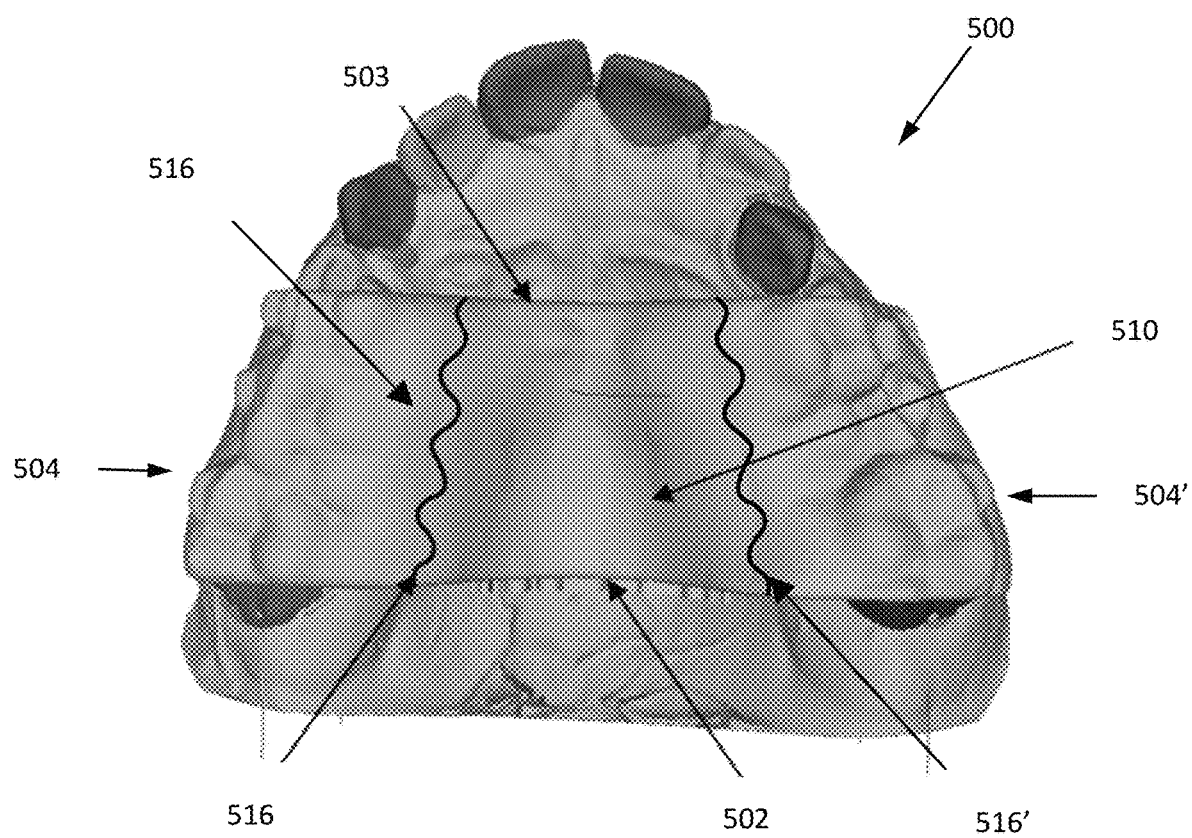
FIG. 5 illustrates a lingual view of an example palatal expander on an upper jaw, showing junctions with curved joining surfaces.

FIG. 5 shows another example palatal expander 500 (shown on the lingual side 510) that includes junctions 516 and 516' (junction region) having curved joining surfaces. In FIG. 5, the junction regions is sinusoidal and curves back and forth as it extends from the distal to the anterior 503 region of the palatal expander. This configuration can allow for a more robust junction between the regions once the regions are joined together (e.g., via adhesive, weld, and/or other type of connecting agent) compared to flat joining surface. In some cases, the curved joining surfaces have unique curvatures that allow for excluding fitting between matching palatal region 502 and tooth engagement regions 504 and 504'.

Figure 6:
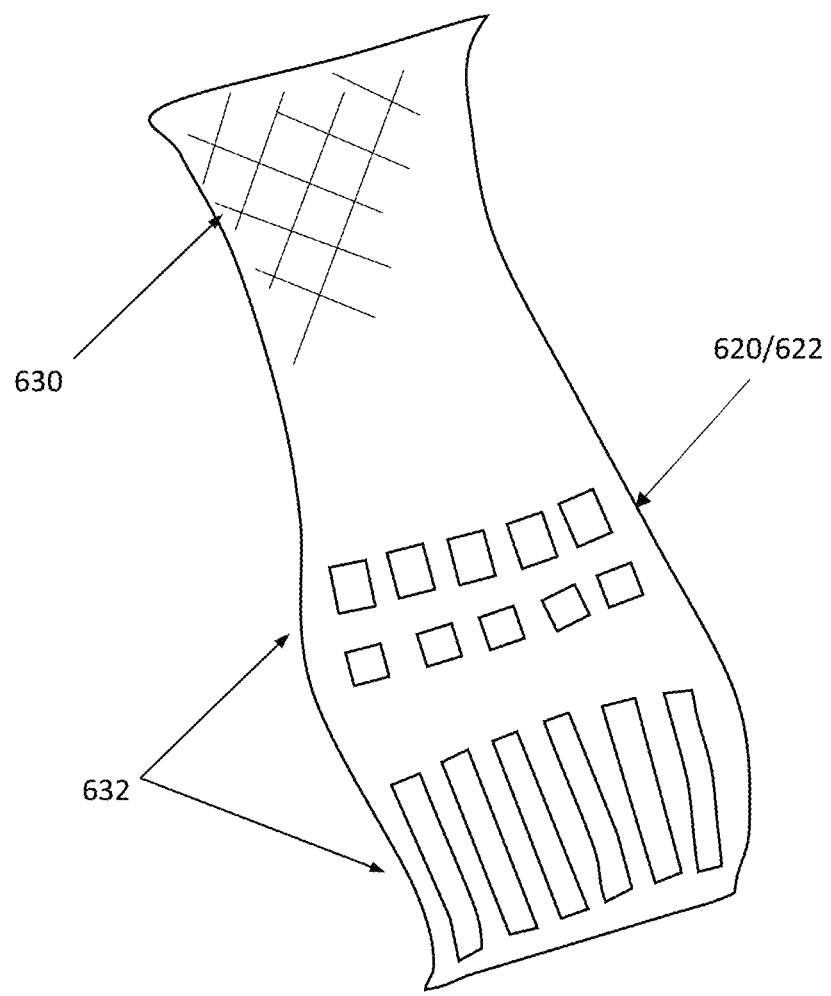
FIG. 6 illustrates an example joining surface of a tooth engagement region or a palatal region, where the joining surface has one or more textures.

The joining surface of a tooth engagement region and/or a palatal region of a palatal expander may include a surface texture to enhance the coupling between the different regions of the palatal expander. FIG. 6 shows examples of joining surfaces 620 of a tooth engagement region or a joining surface 622 a palatal region. The joining surface 620/622 can have one or more surface textures to increase mechanical coupling between the tooth engagement region and palatal region. In this example, the joining surface 620/622 may include a cross-hatch surface pattern 630 (e.g., including a series of crossed raised or indented lines) and/or a geometric pattern 632 (e.g., including raised or indented polygonal, oval, circular shaped surfaces). In some instances, the surface textures form undercut features. In some cases, a raised pattern on a joining surface of a tooth engagement region may correspond to an indented pattern on a joining surface of a palatal region, or vice versa, thereby forming secure engagement between the parts. In some cases, an adhesive (e.g., adhesive resin) is used in conjunction with the surface texture to fixedly couple the tooth engagement region and palatal regions together. For example, indentations within the textured surface may be filled with an adhesive before coupling with the corresponding part. The patterning/texturing can add a mechanical component that helps chemical adhesion. This can be used during printing (or molding) of multiple materials, or different prints (or molds) of various material.

Figure 7:
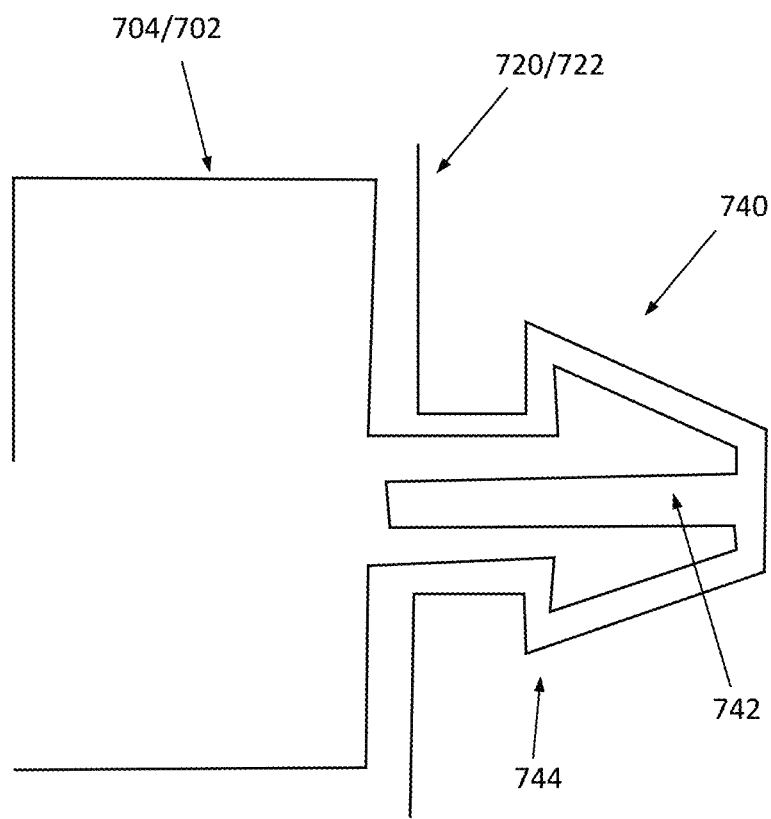
FIG. 7 illustrates an example of a spring-type fastener for coupling a tooth engagement region or a palatal region.

FIG. 7 shows another example of a joining mechanism, in this case, a spring-type fastener 740. The spring-type fastener 740 can be on a joining surface 720 of a tooth engagement region 704 or a joining surface 722 a palatal region 702 of the palatal expander. The spring-type fastener 704 is adapted to be pressed within an opening of the corresponding part (tooth engagement region or palatal region) and be retained within the opening. For example, the center 742 of the fastener 740 can be hollow such that the fastener 740 can compress while entering the opening. Once within the opening, a lip 744 of the fastener 740 retains the fastener 704 within the opening, thereby locking the respective parts together. This configuration may not require an adhesive.

Figure 8:
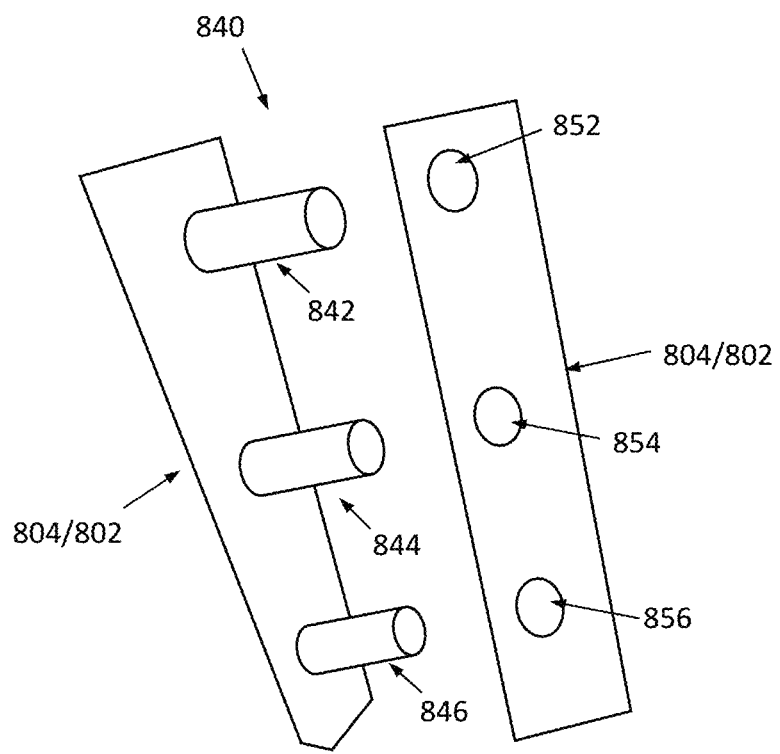
FIG. 8 illustrates an example of a press-fit fastening system for coupling a tooth engagement region or a palatal region.

FIG. 8 shows an example of a press-fit fastening system 840. In some embodiments, a joining surface of the tooth engagement region 804 includes one or more pins 842/844/846 configured to press fit into corresponding holes 852/854/856 of the palatal region 802. In other embodiments, a joining surface of the palatal region 802 includes one or more pins 842 configured to press fit into corresponding holes 844 of the tooth engagement region 804. The pins 842/844/846 and holes 852/854/856 are shaped and sized such that when the pins 842 are pushed within corresponding holes 852/854/856, the corresponding parts 802/804 are held together by friction (interference fit). In some cases, the pins 842/844/846 have different diameters such that they are configured to press fit with holes 852/854/856 having corresponding diameters. This can assure that the parts 802/804 are accurately aligned and oriented with respect to each other when coupled together.

Figure 9:
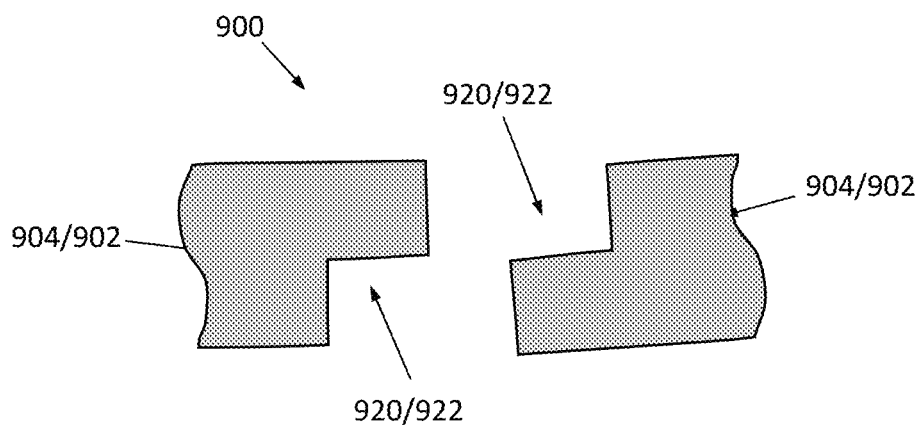
FIG. 9 illustrates an example of an interlocking system for coupling a tooth engagement region or a palatal region.

FIG. 9 shows an example of an interlocking system 900 in which joining surfaces 920/922 of the tooth engagement region 904 and the palatal region 902 have corresponding three-dimensional shapes. Different mechanical features can be fabricated to join IPE sections. Control over the shape of the joining surfaces 920/922 in three dimensions can allow for accurate placement and tight mechanical interlocking of the regions 904/902. In some cases, adhesive is used in conjunction with the interlocking system 900 to couple the regions 904/902.

Figure 10:
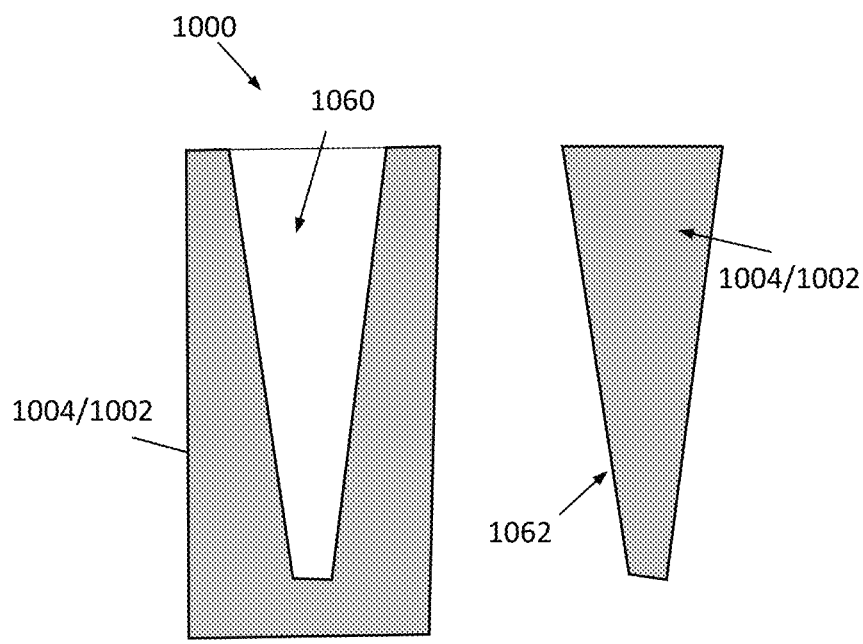
FIG. 10 illustrates an example of a V-shaped press fit system for coupling a tooth engagement region or a palatal region.

FIG. 10 shows an example of a V-shaped press fit system 1000 in which a joining surface of the tooth engagement region 1004 or palatal region 1002 includes a V-shaped opening 1060, and the corresponding tooth engagement region 1004 or palatal region 1002 include a corresponding V-shaped protrusion 1062. The V-shaped opening 1060 and protrusion 1062 can be sized and shaped to create a press-fit (interference fit) coupling, and can assure accurate alignment between the parts 1004/1002. In some cases, the palatal expander includes multiple V-shaped openings 1060 and protrusions 1062.

Figure 11:
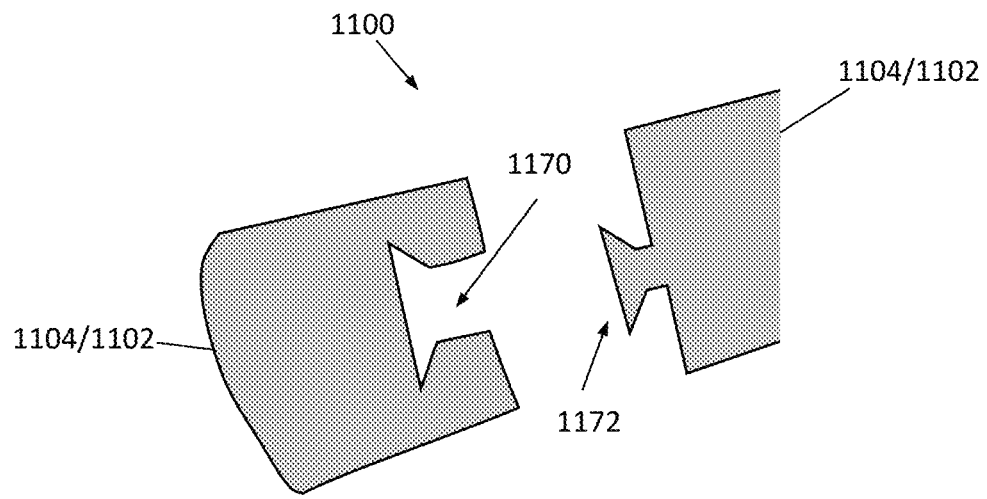
FIG. 11 illustrates an example of a slotted feature system for coupling a tooth engagement region or a palatal region.

FIG. 11 shows an example of a slotted feature system 1100 includes a joining surface of the tooth engagement region 1104 or palatal region 1102 includes a slot 1170, and the corresponding tooth engagement region 1104 or palatal region 1102 include a correspondingly shaped protrusion 1172. The slot 1170/protrusion 1172 may have corresponding dove-tailed shapes and be adapted to slide and lock together.

When forming the various regions of the dental devices, factors such as material shrinkage may be accounted for. For example, polymer materials may shrink once they are cured and/or cooled/hardened. Different types of polymers and/or polymer composites may shrink to different extents based on the chemical composition and/or the method of fabrication. Thus, the dimensions of parts made of different materials may change to different extents based on these shrinkage differences. To account for such differences, the dimensions of the part during fabrication (e.g., printing and/or molding) can factor in an expected amount of shrinkage. In some additive manufacturing fabrication processes, the dimensions of the computer model of a first part made of a first material may be adjusted to account for a higher or lower expected shrinkage relative to a second part made of a second material to which the first part is to be coupled with. In some molding processes, the dimensions of the mold for a first part made of a first material may be adjusted to account for a higher or lower expected shrinkage relative to a second part made of a second material. The relative degree of shrinkage of a first material and a second material can be determined by fabricating a first test part using the first material and a second test part (having the same dimensions as the first part) using the second materials, then measuring dimensional changes in each of the test parts. A relative shrinkage factor can be calculated based on whether one of the test parts shrinks more than the other. In some cases, the relative shrinkage factor may depend at least in part on the fabrication method. For example, a first part formed using a first fabrication process (e.g., additive manufacturing or molding) may shrink more or less than a second part formed using a second fabrication process (e.g., additive manufacturing or molding) that is different than the first fabrication process. Once the relative shrinkage factor is determined, the dimensions of the computer model or mold can be adjusted accordingly.

Figure 12:
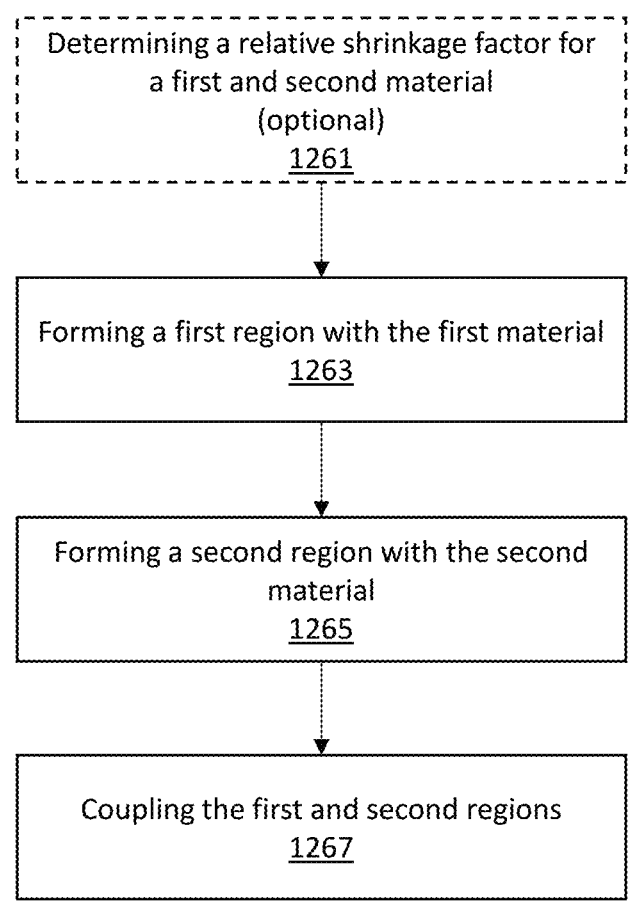
FIG. 12 illustrates a flowchart indicating an example process of forming a dental device from separately formed regions.

FIG. 12 shows a flowchart indicating an example process of forming a dental device from separately formed parts. At 1261, optionally, a relative shrinkage factor for a first material relative to a second material is determined. The relative shrinkage factor can be determined based on different degrees of expected shrinkage for the different materials. The dimensions of computer model and/or mold used to form a first region (e.g., palatal region) and a second region (e.g., tooth engagement region) may take into account the relative shrinkage factor.

At 1263, one or more first regions (e.g., palatal region) of the dental device (e.g., palatal expander) is formed using a first material. Any fabrication techniques may be used. In some cases, an additive manufacturing process and/or a molding process is used. The first material may be chosen based at least in part on rigidity. In the case of a palatal expander, the first material should have a sufficiently high rigidity to provide a desired force to expand the patient's palate according to palate expanding treatment plan. The first material may also have some compliance to balance the load deflection for patient comfort. The rigidity and flexibility of the first and second materials may be chosen based on a combination of initial flexural modulus and remaining flexural modulus of the first and second materials.

At 1265, one or more second regions (e.g., tooth engagement region) of the dental device (e.g., palatal expander) is formed using a second material. Any fabrication techniques may be used. In some cases, an additive manufacturing process and/or a molding process is used. In the case of palatal expanders, aligners and attachment template devices, the second region may correspond to tooth engagement regions that includes cavities shaped and sized in accordance with corresponding teeth so that the device registers with the patient's teeth, thereby correctly aligning the device with respect to the patient's dentition and/or jaw. The second material may be less rigid than the first material. The second material may be chosen based at least in part on flexibility. For example, the second material should have a sufficiently high flexibility to bend while the patient fits the device on the teeth and removes the device from the teeth. This can allow for easier placement and removal of the device. In some cases, the second material has an elongation at break measurement (ratio between changed length and initial length after breakage) of greater than 10%. In some embodiments, each of the tooth engagement regions are formed using a different material (e.g., a second material and a third material). Note that forming the palatal region 1263 and forming the tooth engagement regions 1265 may be performed sequentially in any order, or in parallel.

At 1267, the first region is coupled to the second region. In some embodiments, the coupling involves using one or more adhesive materials, such as one or more polymer adhesives. Joining surfaces of the first and/or second regions of the device may include indentations, protrusions and/or a textured surface to increase the adhesion force and/or to assure proper alignment of the different regions. In some embodiments, the coupling involves using one or more fastening features of the first and/or second regions. Examples of fastening features may include a spring-type fastening system, a press-fit fastening system, an interlocking system, a V-shaped press-fit fastening system and/or other fastening systems. The fastening features may or may not be used with adhesive.

Figure 13:
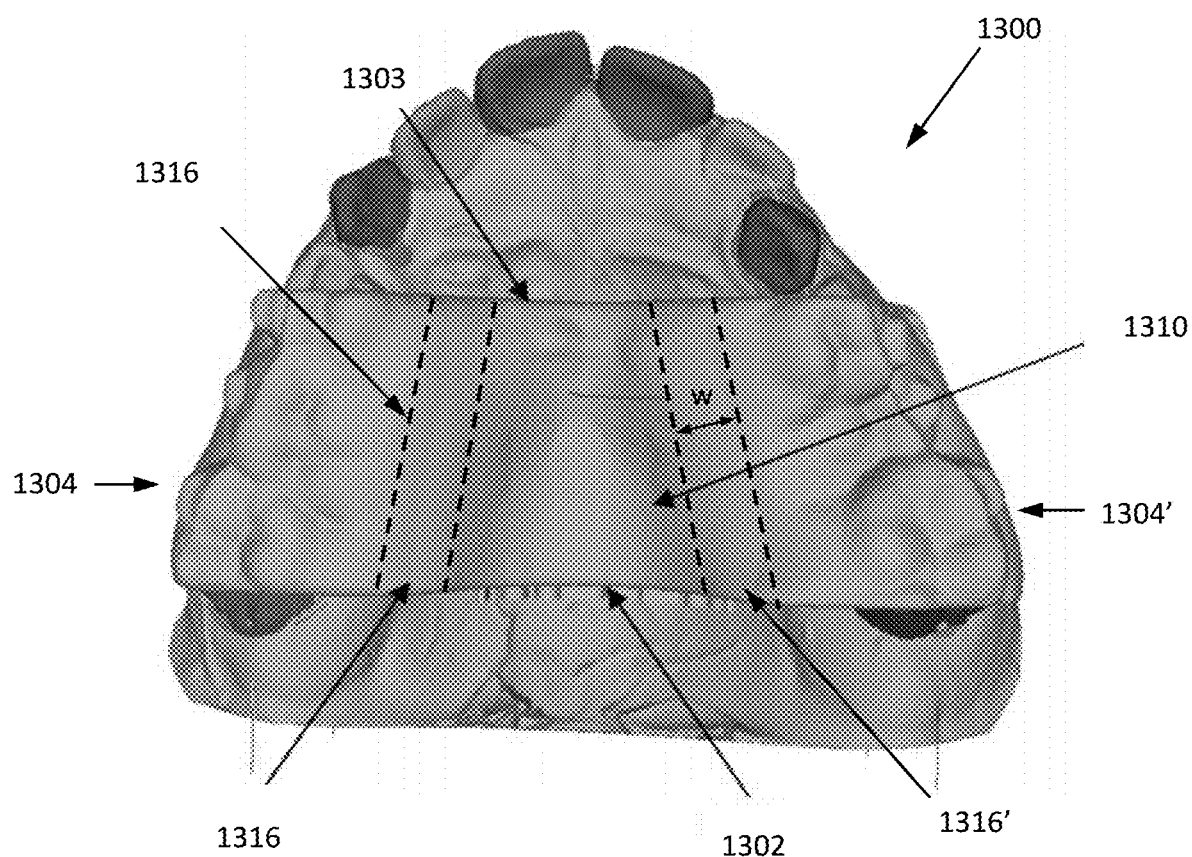
FIG. 13 illustrates a lingual view of an example palatal expander on an upper jaw, showing transitional regions between a palatal region and tooth engagement regions.

In some embodiments, the transition between the different regions of the palatal expander is graduated such that a transition region between the different regions has combined materials of the different regions. FIG. 13 shows a lingual side 1310 of an example palatal expander 1300 that includes two transition regions 1316 and 1316' extending roughly posteriorly to anteriorly 1303. A first transition region 1316 is between a first tooth engagement region 1304 and a palatal region 1302. A second transition region 1316' is between a second tooth engagement region 1304' and the palatal region 1302. In some embodiments, the palatal region 1302 is made of a first material (e.g., first type of polymer or mixture of polymers) and the first and second tooth engagement regions 1304 and 1304' are made of a second material (e.g., second type of polymer or mixture of polymers) different than the first material. In some embodiments, the palatal region 1302 is made of a first material, the first tooth engagement region 1304 is made of a second material, and the second tooth engagement region 1304' is made of a third material, where the first, second and third materials are different from each other.

The transition regions 1316 and 1316' correspond to regions that includes a mixture of materials to provide a smooth material transition between the different regions of the palatal expander 1300. For example, the first transition region 1316 can include a combination of the material of the palatal region 1302 (e.g., first material) and a material of the first tooth engagement region 1304 (e.g., second material). Likewise, the second transition region 1316' can include a combination of the material of the palatal region 1302 (e.g., first material) and a material of the second tooth engagement region 1304' (e.g., second material or third material). The first and second materials may be integrated with each other. Since the transition regions 1316 and 1316' includes a mixture of materials from adjacent regions, the transition regions 1316 and 1316' can provide robust adhesion of the adjacent regions. The mixture may be a homogenous mixture of the multiple polymers.

A width (w) of each of a transition region may vary depending on desired physical characteristics of the palatal expander 1300. In some embodiments, the width (w) ranges from about 0.05 millimeters (mm) to about 10 mm.

In some embodiments, the material change within the transition regions 1316 and 1316' is gradual. For example, if the palatal region 1302 is made of a first material and the first tooth engagement region 1304 is made of a second material, the transition region 1316 may have a gradually decreasing amount of the first material and increasing amount of the second material traveling along a path within the transition region 1316 toward the tooth engagement region 1304 and away from the palatal region 1302.

Figure 14A:
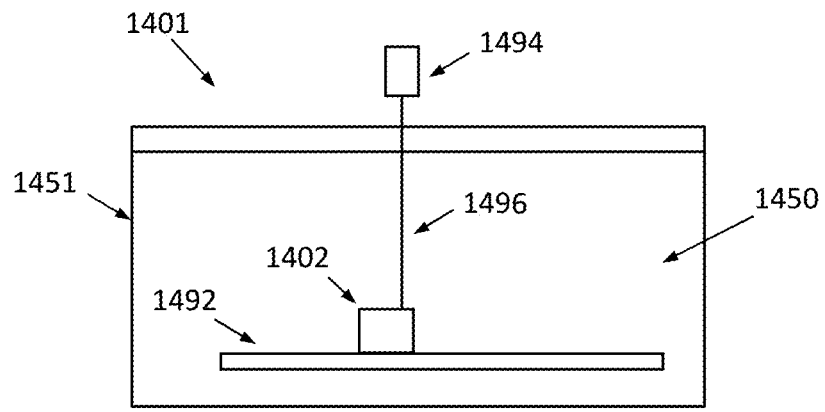
FIGS. 14A-14C illustrate an example process for forming a dental device using a vat-based printing system.
Figure 14B:
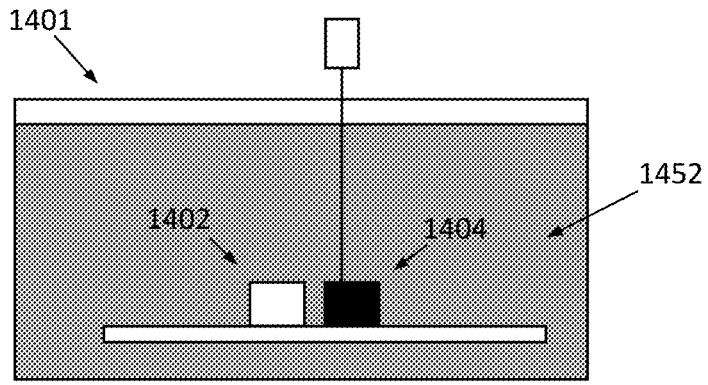
Figure 14C:
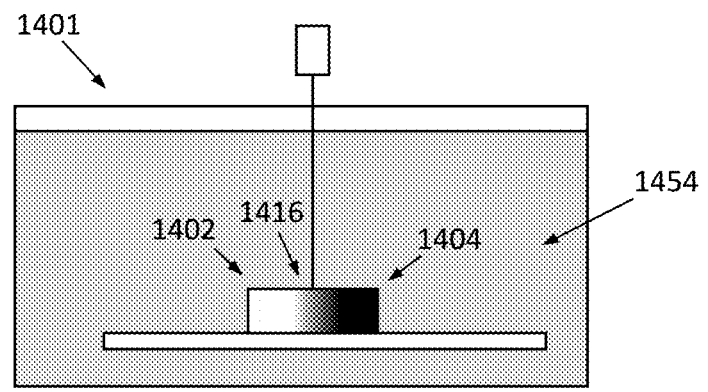

Methods of forming a dental device having transition regions with mixed materials may vary. In some embodiments, an additive manufacturing technology is used, such as those based on vat-based additive manufacturing techniques or jet printing (ink jet printing) techniques. FIGS. 14A-14C shows an example process for forming a dental device using a vat-based printing system 1441. The system 1441 includes vat 1451 (or tank) that contains a first photo-curable material 1450 in liquid form, which includes a monomer and/or oligomer for forming a first polymer prior to polymerization. At FIG. 14A, electromagnetic radiation 1496 (e.g., laser beam) from a source 1494 (e.g., laser) selectively cures a region of the photo-curable material 1450 to form a first region 1402 (e.g., palatal region) of a part additively on a platform 1492. The additive process may include any type of additive process, such as one similar to a continuous liquid interface production (CLIP) process. Alternatively or additionally, a mask projection process can be used to form the first region 1402. At FIG. 14B, the first polymer material 1450 is replaced with a second photo-curable material 1452, which includes a monomer and/or oligomer for forming a second polymer, within the vat 1451. The electromagnetic radiation 1496 is used to cure the second photo-curable material 1452 to form aa second region 1404 (e.g., tooth engagement region) made of the second polymer material. At FIG. 14C, the vat 1451 is filled with a mixture 1454 of the first and second photo-curable materials to form a transition region 1416 (e.g., transition region) of the part. In this case, forming the transition region 1416 joins the first region 1402 and the second region 1404. The order of forming the different regions 1402, 1404 and 1416 of the part may vary. For example, any of the regions 1402, 1404 and 1416 may be formed first, second or last. In some embodiments, the transition region 1416 is formed using multiple steps where the vat 1451 is changed multiple times with different ratios of the first and second polymer materials to create a more refined gradient transition in the transition region 1416. This can be part of an industrial process, particularly a mass-scalable industrial process.

The choice of polymers will be based on physical characteristics such as rigidity, flexibility and/or expansion-force-exerting properties as described herein. In some cases, the polymers are based on the miscibility of the photo-polymer precursors with each other in the mixture for forming the transition regions. Table 1 shows various example polymers used to make different portions of a transition region. In some cases, the polymers/polymer precursors are custom made and not commercially available.

TABLE 1

| | Polymer | Percentage |
|---|---|---|
| Mixture A | Urethane-based cross linker with a high Tg | 60% |
| | Elastomeric like photopolymer with a high elongation at break | 40% |
| | photo-initiator | +1% |
| Mixture B | Urethane-based cross linker with a high Tg | 70% |
| | Elastomeric like photopolymer with a high elongation at break | 30% |
| | photo-initiator | +1% |
| Mixture C and D | Elastomeric like photopolymer with a high elongation at break | 35% |
| | Urethane-based cross linker with a high Tg | 15% |
| | Mono-functional reactive diluent | 50% |
| | photo-initiator | +1% |

Figure 15:
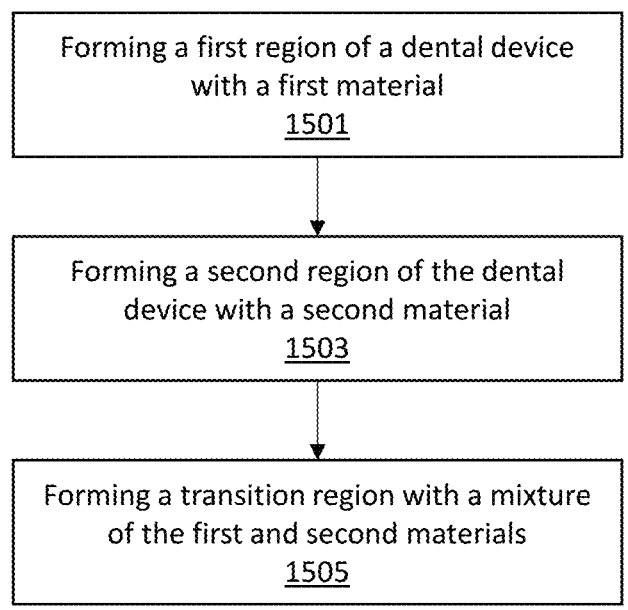
FIG. 15 illustrates a flowchart indicating an example process of forming a dental device having one or more transition regions.

FIG. 15 shows a flowchart indicating an example process of forming a dental device having one or more transition regions. The dental device may be any of a number of types of dental devices, such as a palatal expander, dental aligner (e.g., with a mandibular advancement block) or dental attachment template for placement and bonding of attachments to the patient's teeth. At 1501, one or more first regions of the dental device is formed using a first material. For a palatal expander, the first material may be a relatively rigid material for forming a palatal region of the device. For a dental aligner, the first material may be a relatively rigid material for structures where relatively high forces are needed to move teeth (such as a mandibular advancement block). For a dental attachment template, the first material may be a relatively rigid material for the attachment itself and the second material may be a remaining portion of the dental attachment template (e.g., for easier handling and/or shipping safety). In the case of dental attachment templates, the dental attachment template may include tooth engagement regions with cavities that are shaped and sized in accordance with corresponding teeth to position support one or more attachments attached thereto in desired position(s) with respect to one or more teeth. Alternatively or additionally, the one or more attachments are attached to and hang from a frame that positions the attachments with respect to the desired position(s). The first material may include one or more types of materials. For example, the first material may include one type of polymer or multiple types of polymers.

At 1503, one or more second regions of the dental device is formed using a second material having different physical characteristics than the first material. For example, the second material may be (less rigid) than the first material. For a palatal expander, dental aligner, or dental attachment template, the second less rigid material may be used to form one or more tooth engagement regions of the device so that the device is easier to remove from teeth by the patient and/or be more comfortable to wear. The second material may include one or more types of materials. For example, the second material may include one type of polymer or multiple types of polymers.

At 1505, one or more transition regions of the dental device includes a mixture of the first and second materials. The transition region(s) may be formed between the first region(s) and second region(s) to couple the first and second regions together. The mixture may have pre-determined relative amounts of the first and second materials. The mixture may include a pre-determined ratio of the first material relative to the second material (e.g., by weight). For example, the mixture may include a first material to second material ratio by weight ranging from about 0.99 to about 0.01 (e.g., 0.99, 0.95, 0.90, 0.85, 0.80, 0.75, 0.70, 0.65, 0.60, 0.55, 0.50, 0.45, 0.40, 0.35, 0.30, 0.25, 0.20, 0.15, 0.10, 0.05 or 0.01). In some cases, the mixture may include one or more additional materials to stabilize the mixture. In some cases, forming the transition region includes forming different portions of the transition region using different relative amounts of the first and second materials. For example, a first portion of the transition region closest to the first region of the device may have a higher first material to second material ratio than a second portion of the transition region closest to the second region of the device. The transition region may include any number of portions having different relative amounts of the first and second materials. For example, the transition region may include from about 1 to 20 (e.g., 1, 2, 3, 4, 5, 6, 7, 8, 9, 10, 11, 12, 13, 14, 15, 16, 17, 18, 19 or 20) portions having different relative amounts of the first and second materials. The number of portions having different relative amounts of the first and second materials can be chosen based on how well the transition region(s) can couple the first and second regions of the device together and/or desired performance. For instance, more portions of the transition region can be used to provide a more gradual gradient of material change and less of a sharp contrast of material change.

Figure 16A:
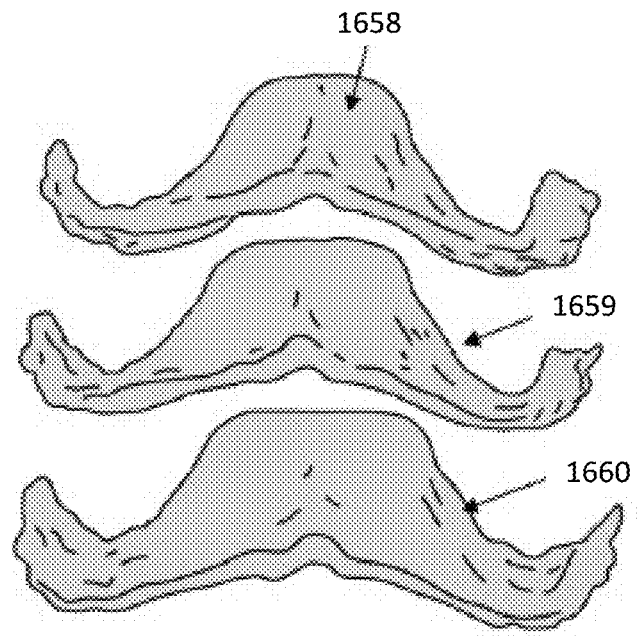
FIG. 16A illustrates a series of palatal expanders that are configured to progressively expand the suture (e.g., the expanders shown in FIG. 16A may be examples taken from an entire sequence, e.g., of 8 or more expanders, and do not necessarily represent three immediately sequential expanders).
Figure 16B:
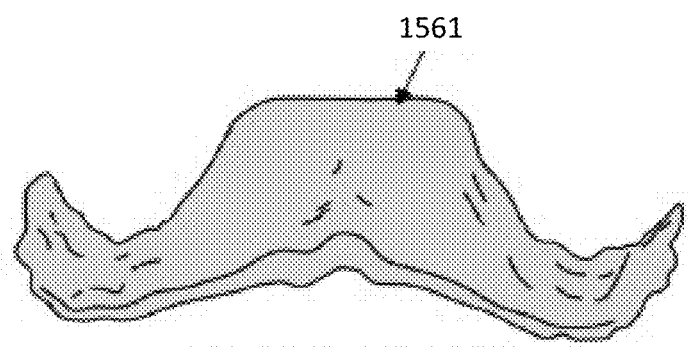
FIG. 16B illustrates a passive holder (e.g., retainer) that may be worn, for example, after the series of FIG. 16A has completed expanding the patient's palate.

The devices described herein may be configured as a system including a series of palatal expanders that progressive expand the patient's palate and/or a passive holder (e.g., retainer) to be worn after the series has widened the palate. For example, FIGS. 16A and 16B illustrate example components of such system. FIG. 16A shows an example of a series of palatal expanders that get progressively broader. For example, an initial upper palatal expander 1658 may have narrower palatal region than the intermediate palatal expander 1659 and a final palatal expander 1660. FIG. 16C illustrate an example of a passive holder (e.g., retainer) 1661 that may be worn after the series has completed expanding the patient's palate. In this example, the palatal expander retainer 1661 is similar or identical to the last of the palatal expanders in the sequence, although it may have a different configuration.

As mentioned above, a palatal expander as described herein can be one of a series of palatal expanders (incremental palatal expanders) that may be used to expand a subject's palate from an initial size/shape toward a target size/shape. For example, the methods and improvements described herein may be incorporated into a palatal expander or series of palatal expander as described, for example, in US20190314119A1, herein incorporated by reference in its entirety. A series of palatal expanders may be configured to expand the patient's palate by a predetermined distance (e.g., the distance between the molar regions of one expander may differ from the distance between the molar regions of the prior expander by not more than 2 mm, by between 0.1 and 2 mm, by between 0.25 and 1 mm, etc.) and/or by a predetermined force (e.g., limiting the force applied to less than 180 Newtons (N), to between 8-200 N, between 8-90 N, between 8-80 N, between 8-70 N, between 8-60 N, between 8-50 N, between 8-40 N, between 8-30 N, between 30-60 N, between 30-70 N, between 40-60 N, between 40-70 N, between 60-200 N, between 70-180 N, between 70-160 N, etc., including any range there between).

The palatal region may be between about 1-5 mm thick (e.g., between 1.5 to 3 mm, between 2 and 2.5 mm thick, etc.). The occlusal side may have a thickness of between about 0.5-2 mm (e.g., between 0.5 to 1.75 mm, between 0.75 to 1.7 mm, etc.). The buccal side may have a thickness of between about 0.25-1 mm (e.g., between 0.35 and 0.85 mm, between about 0.4 and 0.8 mm, etc.).

The dental devices described herein can include any of a number of features to facilitate the expansion process, improve patient comfort, and/or aid in insertion/retention of the dental devices in the patient's dentition. Examples of some features of dental devices are described in U.S. Patent Application Publication No. 2018/0153648A1, filed on Dec. 4, 2017, which is incorporated herein by reference in its entirety. For example, any of the dental devices described herein may include any number attachment features that are configured to couple with corresponding attachments bonded to the patient's teeth. The dental devices may have regions of varying thickness. In any of the dental devices described herein can have varied thicknesses. For example, the thickness of a palatal region may be thicker or thinner than the thickness of tooth engagement regions. The palatal region of any of the palatal expanders may include one or more cut-out regions, which may enhance comfort and/or prevent problems with speech.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, computer models (e.g., for additive manufacturing) and instructions related to forming a dental device may be stored on a non-transitory computer-readable storage medium.

The methods and apparatuses described herein may use different material, and in particular, may use different photopolymers with different material behaviors within the same device or region of a device. For example, as described above, in some variations the region of a device that engages with the subject's teeth (e.g., the "wings") may be different from the region of the device that engages with the palate (e.g., the center, central, or palatal region); in some variations these different regions may be formed of different photopolymers that may have different properties.

By using different material properties within a single device, all of the material property requirements for a dental appliance may be achieved. For a single, e.g., printed, appliance. FIG. 17 illustrates one example of an appliance (a palatal expander) having flexible wing (tooth-engaging) regions 1701 that may permit low insertion forces, and may have a high modulus and a high remaining stress for the apparatus, and in particular the palatal region 1703 to achieve palatal movement. This could be achieved by changing the material during additive manufacturing (e.g., for a vat-based 3D printing process) or by changing the resin composition (e.g., for jetting-based additive manufacturing processes).

In some variations the direction of printing may be selected. For example, the printing direction for a vat-based additive manufacturing process maybe from the wing region to the palatal region and back again, so that the wing region (more flexible tooth engaging region) has a higher elongate. The modulus and the remaining stress in the wings may be lower than that for the palatal region as the wing may have less impact on the required palatal movement. The increase flexibility of the wings may allow them to be applied to the teeth with lower insertion forces. In some variation the device may be printed so that the left wing portion is printed first (from the left-to-right direction), and once the printing has extended to a height (e.g., $h1$ in FIG. 17) that extends into the palatal region 1703, the resin may be changed and printed with a higher modulus material to a second height of $h2$ forming the palatal region. A second transition may be made to form the second (e.g., left) wing region printing in the first, lower modulus material, to the third height $h3$. Thus, any of the apparatuses described herein may include material transition regions or boundaries between lower modulus (more flexible) material and higher modulus (less flexible) material that extend in parallel lines from the front (anterior) of the device to the back (posterior) of the device; these boundaries may overlap with both wing (tooth-engaging) and palatal regions of the appliance. A second region of the device formed of a higher modulus material may extend a constant height (diameter) between the wing regions formed of a lower modulus material and may include the palatal region.

The method and features described herein may also include or be included as part of an attachment template (dental attachment template) for placing one or more dental attachments onto a subject's teeth, e.g., to help assist in securing a dental appliance to the subject's teeth. For example, described herein are attachment templates in which the dental attachment template includes stiffer (more rigid) regions that are configured to break away or apparat from more compliant regions configured as tooth-engagement (e.g., support) regions that may position the one or more attachments at predetermined and appropriate locations on the teeth. For example, the methods and features described herein may be used to modify a dental attachment structure as described in US20190298494A1, herein incorporated by reference in its entirety.

For example, the apparatuses and methods described herein may include dental attachment templates and methods of making and using them that include forming the attachment portions from a stiffer material, such as a material having a stiffness (e.g., Young's modulus) that is higher than more compliant region. For example the Young's modulus of the attachment portions may be formed of a material, as described herein, having a Young's modulus of 5 GPa or greater (e.g., 7 GPa or greater, 8 GPa or greater, 9 GPa or greater, 10 GPa or greater, 11 GPa or greater, 12 GPa or greater, 13 GPa or greater, 14 GPa or greater, 15 GPa or greater, 20 GPa or greater, 25 GPa or greater, between 5 GPa and 1000 GPa, etc.). Thus, this may result in stiffer regions for the attachments. The more compliant regions, such as the tooth-engagement regions may have a Young's modulus of less than the Young's modulus of the attachment(s), such as a Young's modulus of 10 GPa or less, 9 GPa or less, 8 GPa or less, 7 GPa or less, 6 GPa or less, 5 GPa or less, 4 GPa or less, 3 GPa or less, 2 GPa or less, 1 GPa or less, 0.5 GPa or less, 0.1 GPa or less, etc.). Thus, the tooth-engagement and attachment positioning portions of the apparatus may generally have a lower Young's modulus as compared to the attachment(s).

Any of these apparatuses may include a junction region between the attachment(s) and the tooth-engaging region, as described above. In some examples, the apparatus may include one or more interface printing areas. In general, these apparatuses may be formed as part of a single 3D printing process (e.g., in a single vat).

Figure 17A:
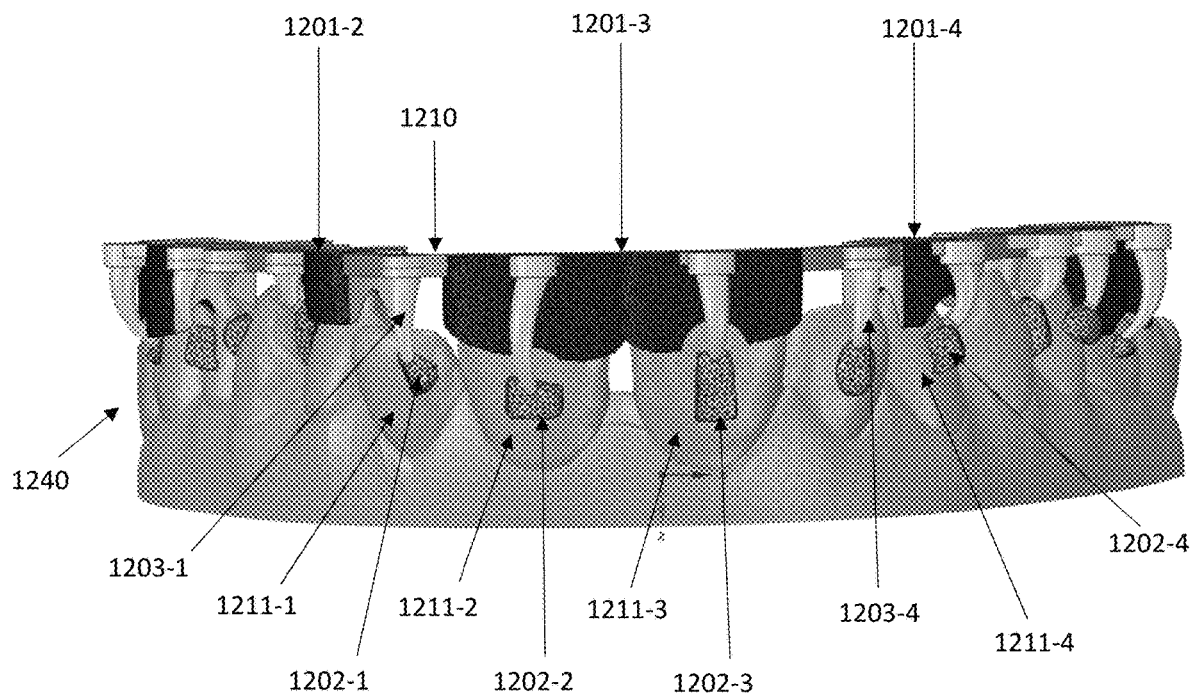
FIG. 17A illustrates a front view of a dental attachment placement structure that includes a frame and may be fabricated or configured as described herein.
Figure 17B:
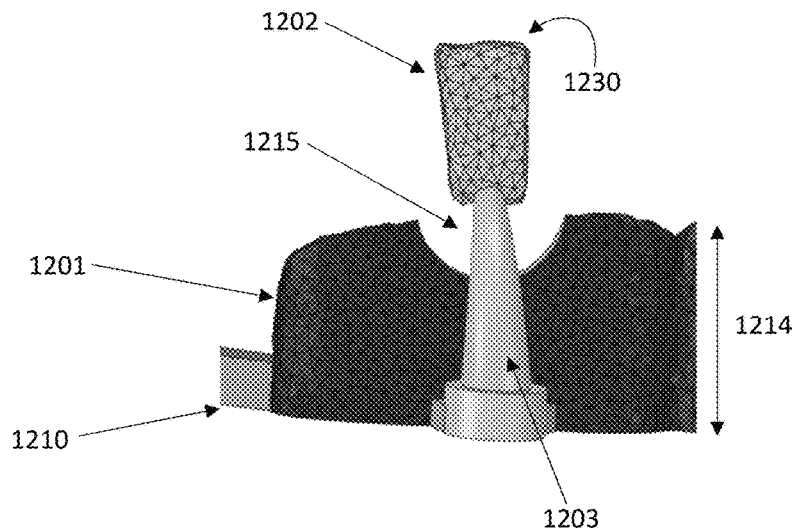
FIG. 17B illustrates a close-up view of a dental attachment of the attachment placement structure of FIG. 17A.
Figure 17C:
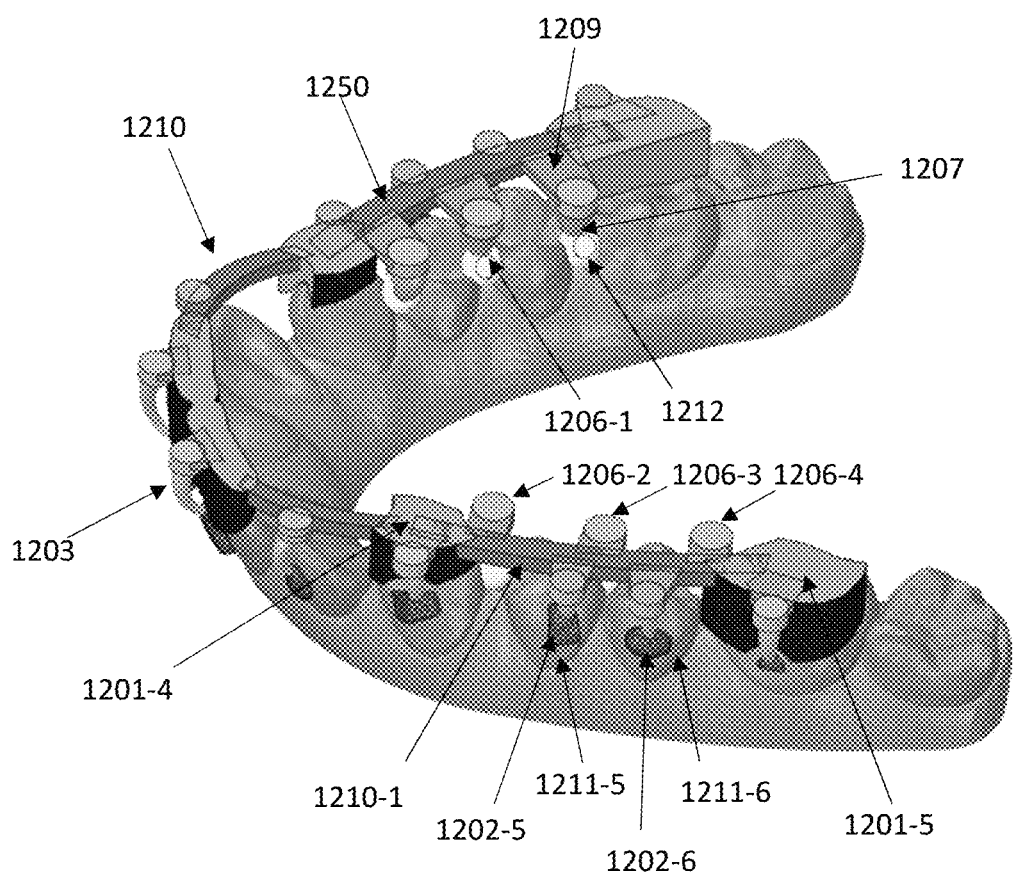
FIG. 17C illustrates a perspective side view of the dental attachment placement structure of FIG. 17A.
Figure 17D:
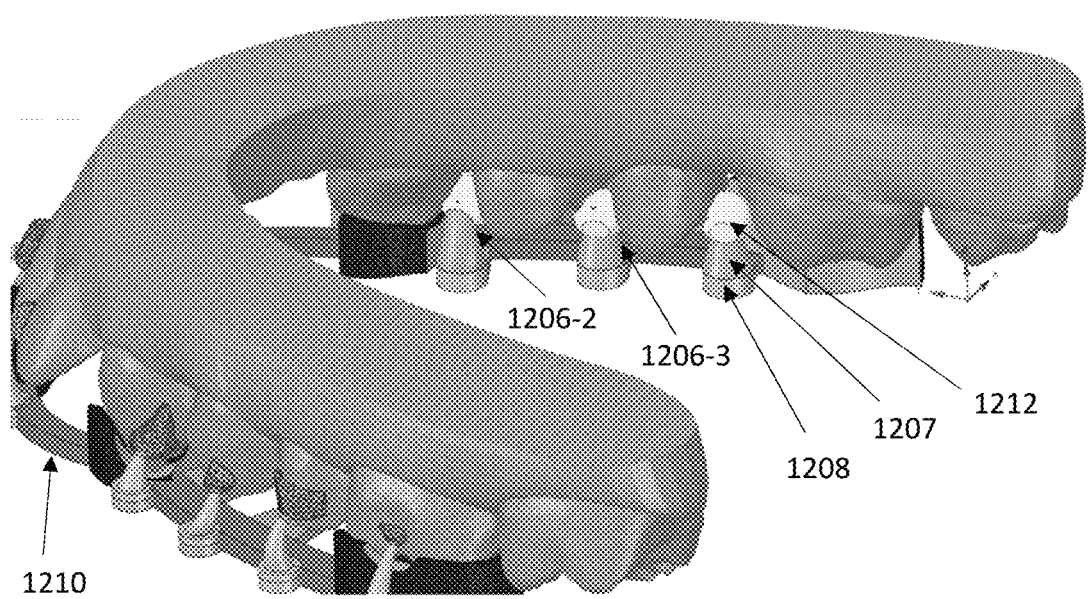
FIG. 17D illustrates an alternative perspective side view of the dental attachment placement structure of FIG. 17A.
Figure 17E:
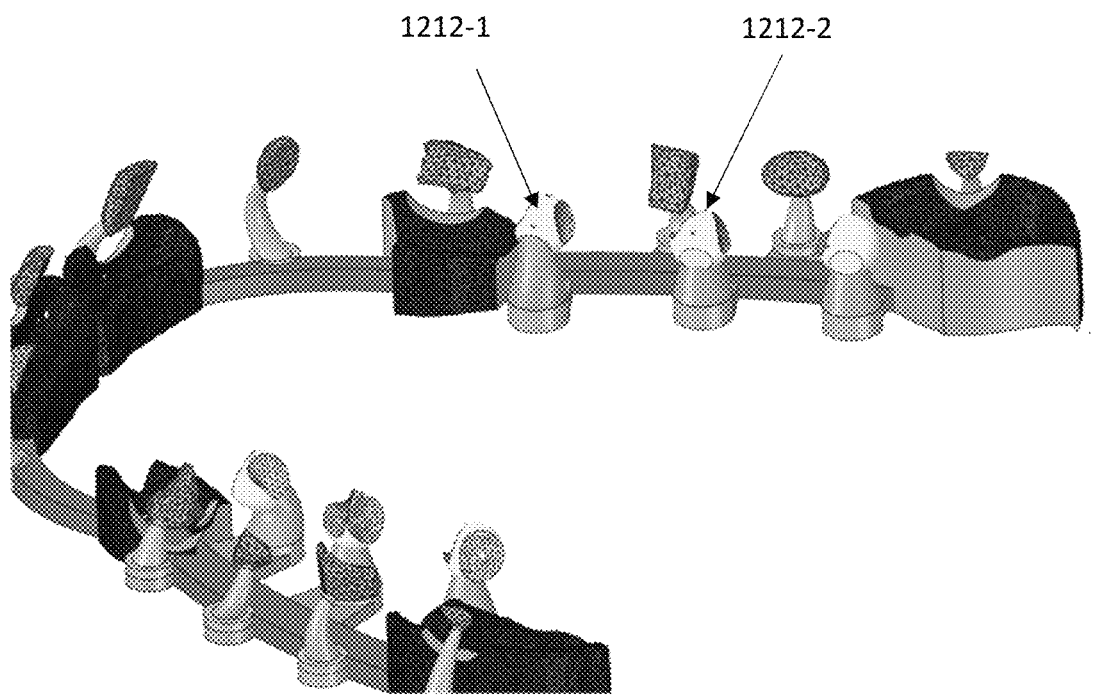
FIG. 17E illustrates a perspective side view of the dental attachment placement structure of FIG. 17A without a dental arch.
Figure 17F:
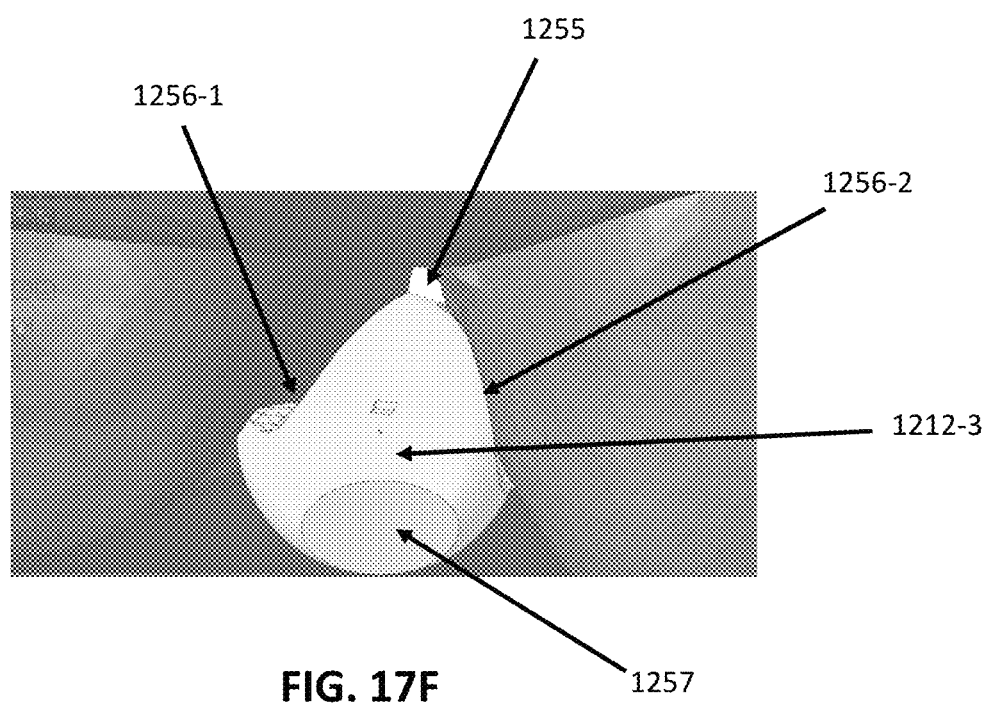
FIG. 17F illustrates a close-up view of a contact portion of a retention support of the dental attachment placement structure of FIG. 17A.
Figure 17G:
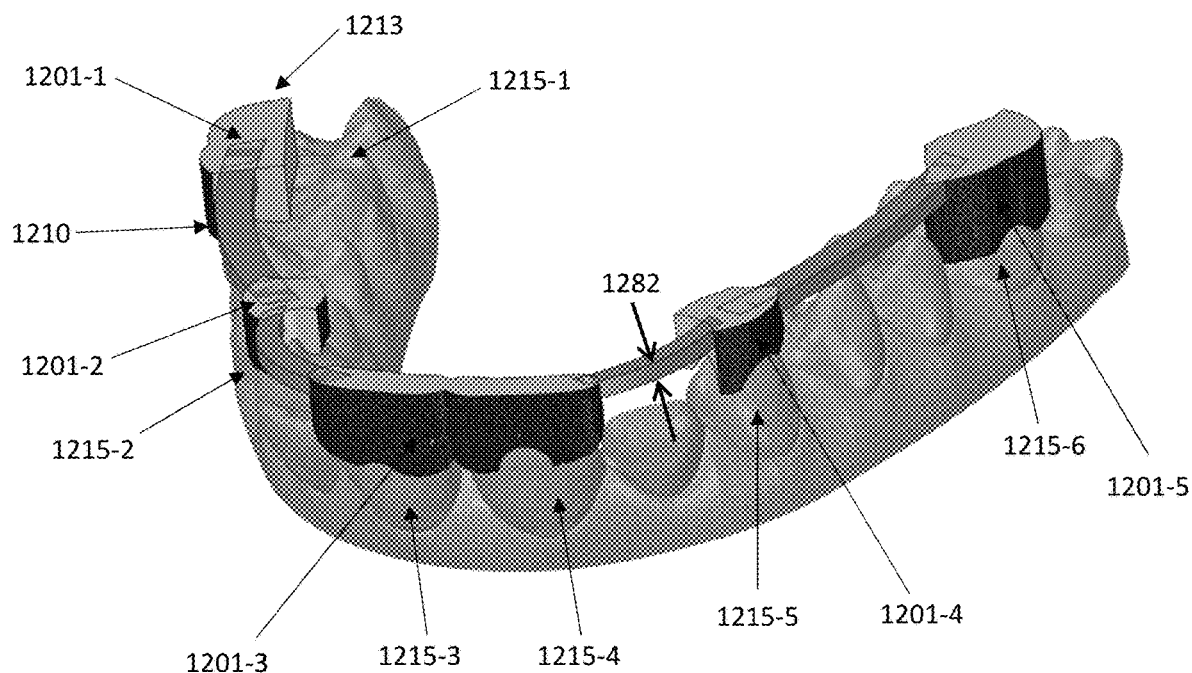
FIG. 17G illustrates a perspective side view of the frame and registration anchors of the dental attachment placement structure of FIG. 17A.
Figure 17H:
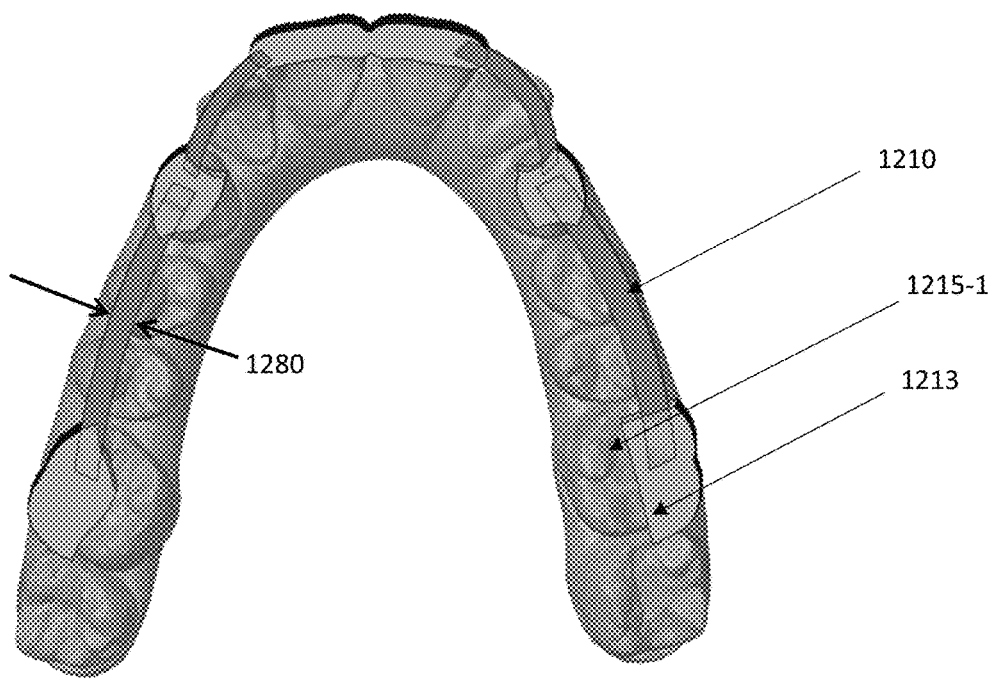
FIG. 17H illustrates an alternative perspective side view of the frame and registration anchors of the dental attachment placement structure of FIG. 17A.
Figure 17I:
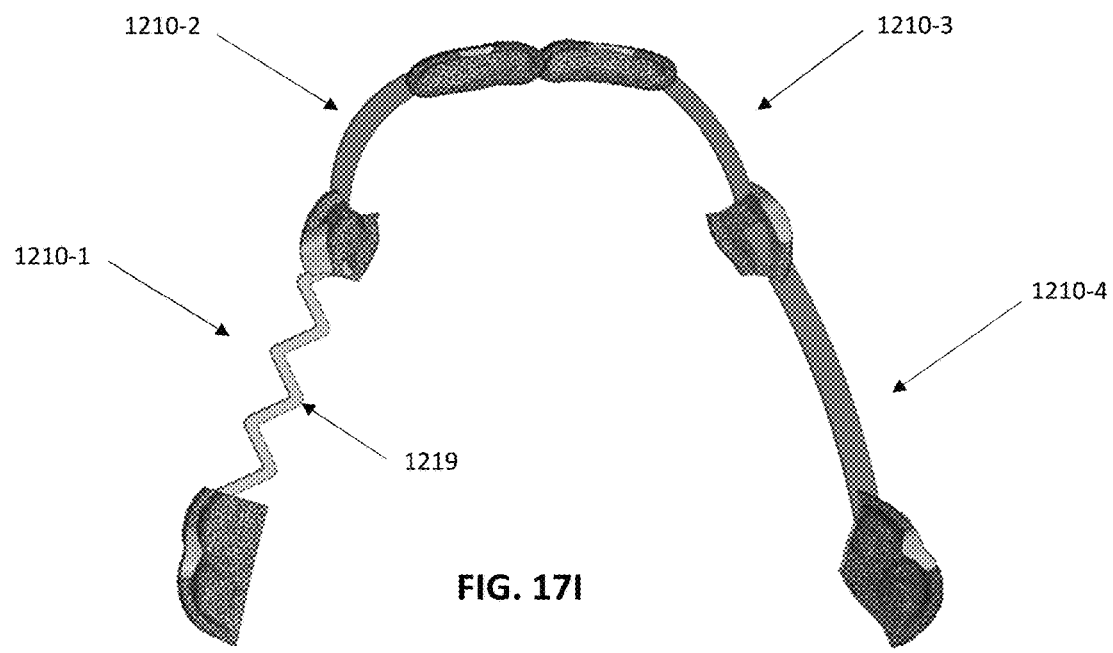
FIG. 17I illustrates an overhead view of an alternative of the dental attachment placement structure of FIG. 17A having a flexible frame portion.
Figure 17J:
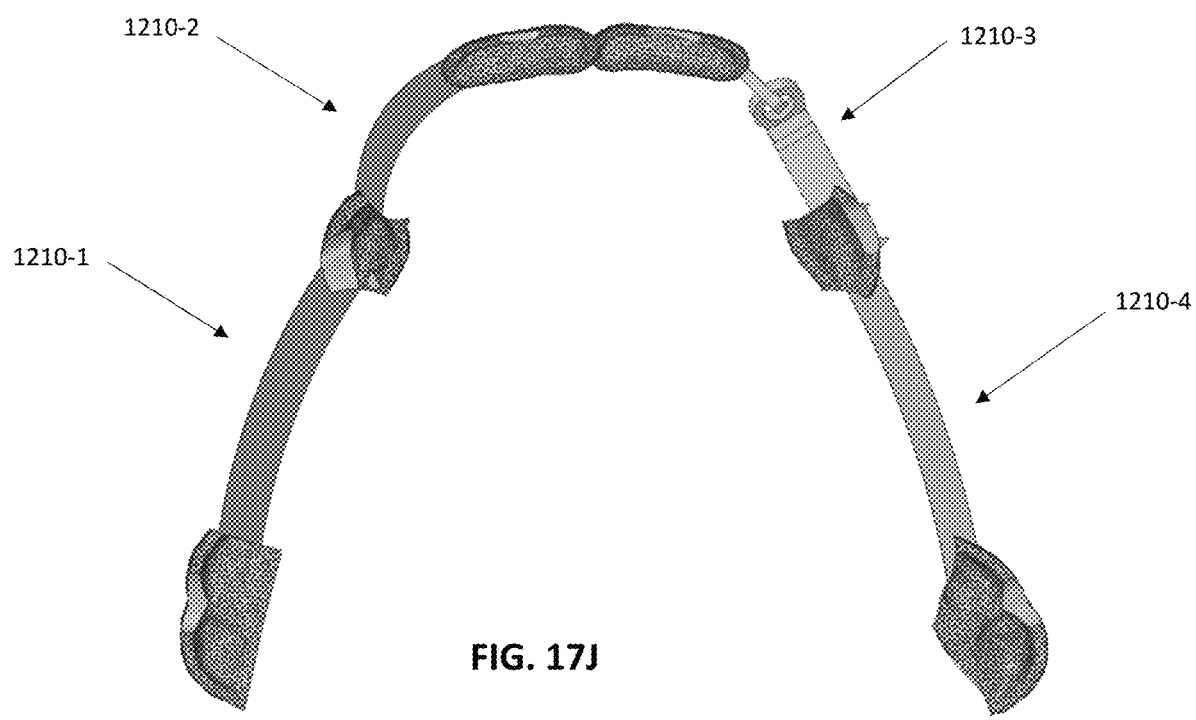
FIGS. 17J and 17K illustrate an overhead view and perspective side views of another alternative of the dental attachment placement structure of FIG. 17A having a flexible frame portion.
Figure 17K:
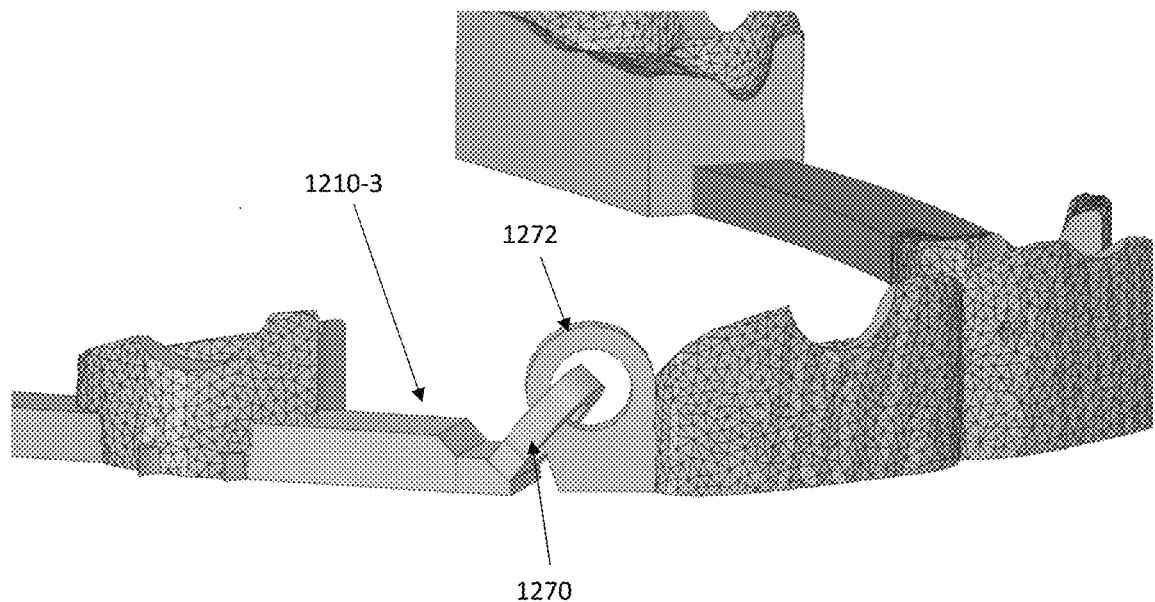
Figure 17L:
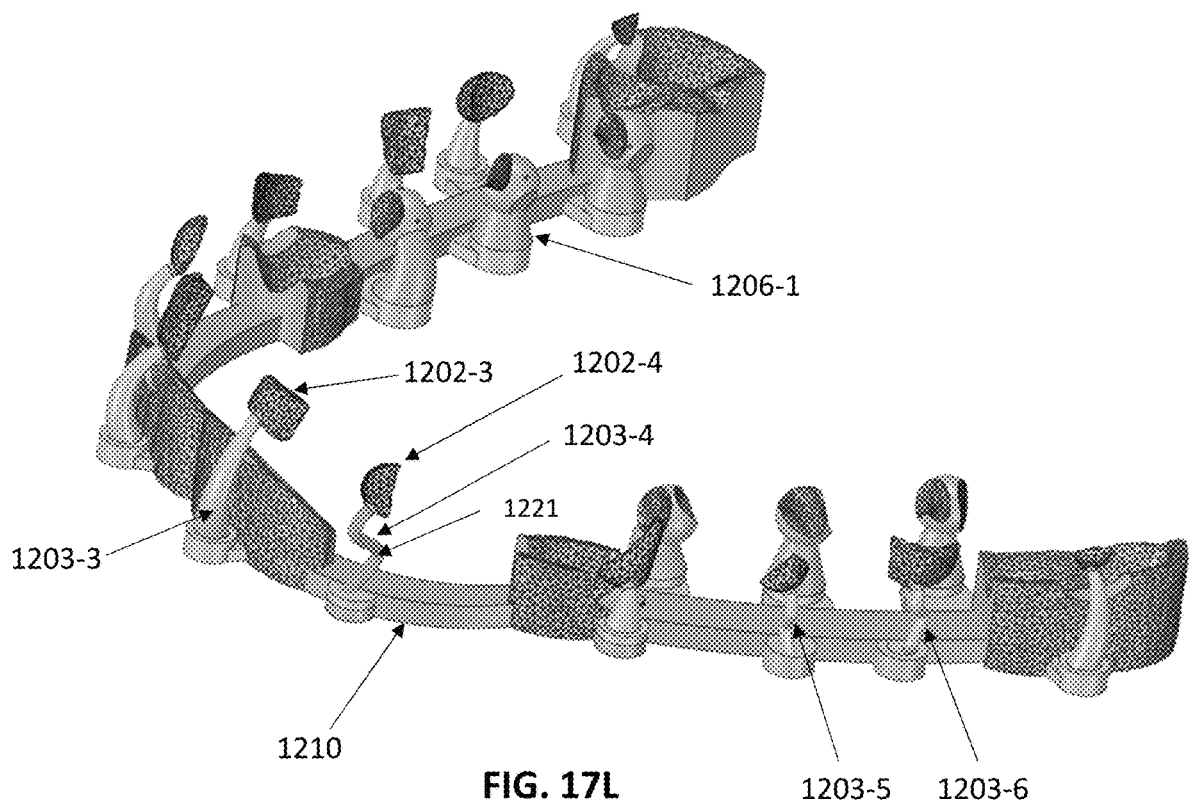
FIG. 17L illustrates a perspective side view of an alternative of the dental attachment placement structure of FIG. 17A having a flexible attachment support.
Figure 17M:
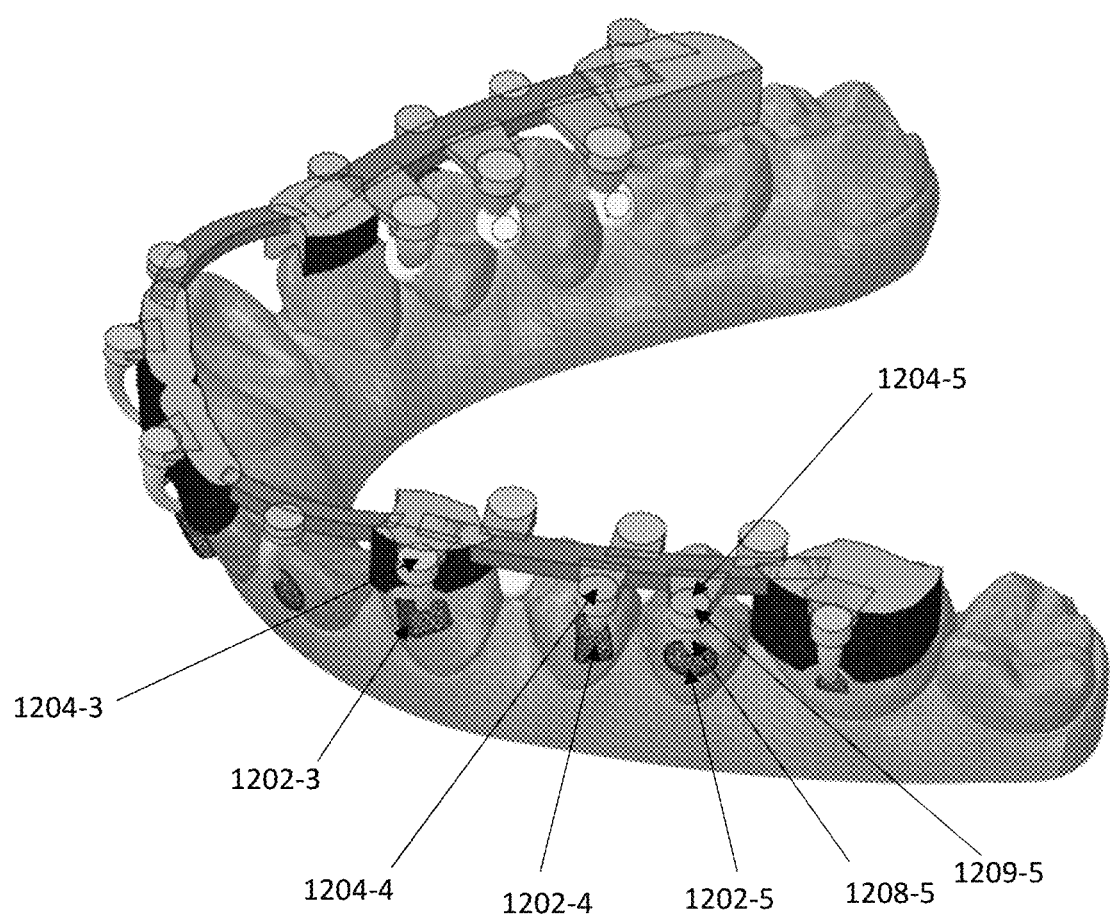
FIGS. 17M and 17N illustrate various perspective side views of the dental attachment placement structure of FIG. 17A showing aspects of the attachment supports.
Figure 17N:
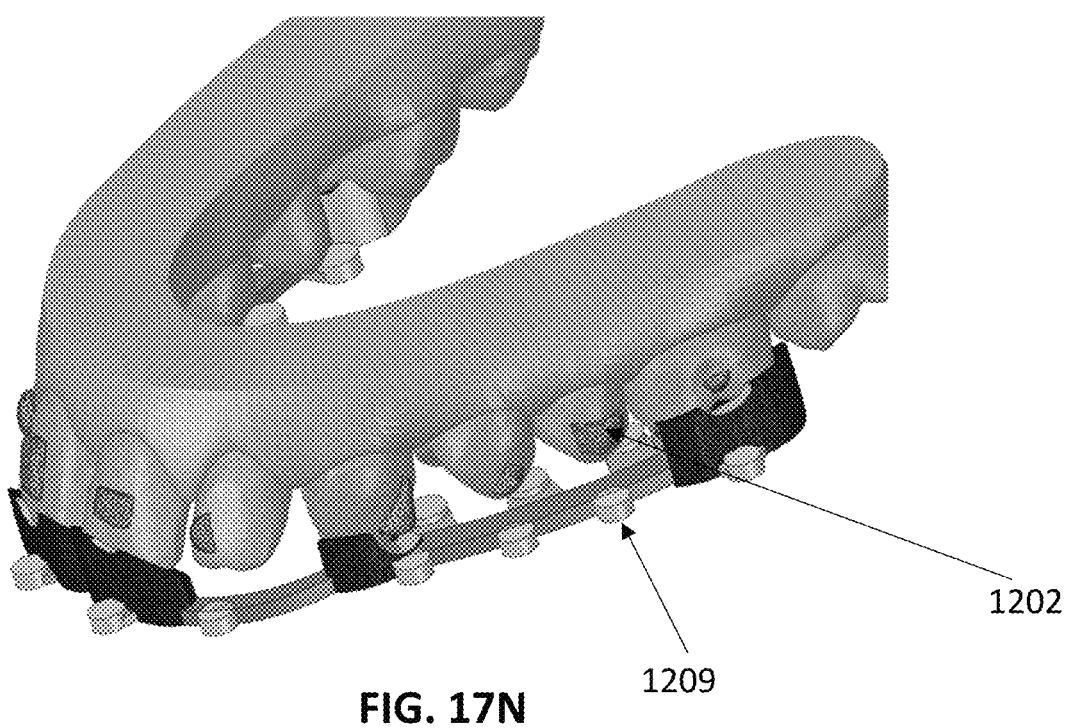

For example, FIGS. 17A-17N illustrate examples of attachments and dental attachment templates that may be formed as described herein. For example, FIG. 17A illustrates a front view of a dental attachment placement structure according to a number of embodiments of the present disclosure. The structure illustrated includes several components that when used together can be beneficial in the accurate placement and orientation of one or more attachments on one or more buccal tooth surfaces of a dental arch 1240. The features illustrated in this figure are a frame 1210 configured to extend over at least a portion of the dental arch. The frame may be a solid structure that follows the shape of the dental arch of the patient, or a portion of the dental arch. The frame can support one or more extending structures that cooperate with the frame to register the one or more dental attachments (examples of which are identified as 1202-1, 1202-2, 1202-3, and 1202-4) to predetermined tooth surface position(s). The dental attachment(s) may be attached to the frame via one or more an attachment supports (examples of which are identified as 1203-1 and 1203-4). This can allow the dental attachment to extend a distance from the frame and to access the predetermined position on a corresponding tooth surface. If multiple attachments are used, the attachment supports may extend in the same direction with respect to the frame. For instance, attachment supports may extend in a downward (or upward) direction from the frame to position the supports below (or above) the frame.

The dental attachment may be removably attached to the attachment support such that the attachment can be detached from the dental attachment placement structure, for example, after the attachment is affixed to the tooth surface. An attachment may be attached to an attachment support at an interface region between the attachment and attachment support. This interface region may be configured for easy detachment. For example, the attachment support may have a thicker end close to the frame that tapers to a lesser thickness at the interface region for easier detachment. In some embodiments, detachment is accomplished using a detachment tool, as described herein. In a number of embodiments, the interface region is sufficiently frangible to allow the attachment to break away from the attachment support without the use of detachment tool. In some cases, a user may be able to detach the attachment by applying a compressive, tensile or pressing force on the attachment (e.g., by the user's hand).

The frame may also include one or more registration anchors (examples of which are identified as 1201-2, 1201-3, and 1201-4) that extend from the frame and that include contact surfaces that register with corresponding one or more teeth. When the contact surfaces of the registration anchor(s) register with corresponding teeth, the dental attachments can also register with the corresponding tooth surfaces. In some cases, the registration anchor contact surface is contoured to complement the undulations and/or grooves of a corresponding surface of one or more teeth. The contoured surface may be adapted to complement the surfaces of any type of one or more teeth, such as one or more incisors, canines, premolars, and molars. The contoured surface may be adapted to complement any side of a tooth, such as one or more lingual, occlusal, buccal, and distal tooth surfaces. In some embodiments, the registration anchor may at least partially encapsulate an incisal edge of a tooth. The registration anchor may and extend over more than one side of a tooth, such as portions of the top (e.g., crown), buccal and/or lingual sides of the corresponding tooth. In the example shown in FIG. 17A, the registration anchors extend over the top and buccal sides of corresponding teeth.

In some cases, the dental attachment is configured to attach to the same tooth as the tooth that the registration anchor is configured to contact. For instance, attachment 1202-4 is aligned with a surface of tooth 1211-4, which is the same tooth that registration anchor 1201-4 is registered with. In some cases, the registration anchor is configured to registered with a different tooth that the tooth that the dental attachment is configured to attach to. For instance, attachment 1202-1 is aligned with a surface of tooth 1211-1, which is different than tooth 1211-2 that registration anchor 1201-3 is registered with. The registration anchor may be configured to registered with multiple teeth. For instance, registration anchor 1201-3 can adapted to registered with surfaces of tooth 1211-2 and tooth 1211-3. When the one or more registration anchors are correctly placed on and registered with corresponding tooth surface(s), the dental attachment placement structure can be properly aligned with the dental arch, and the attachment(s) can be precisely positioned with respect to the tooth surface(s).

FIG. 17B illustrates a close-up view of an attachment portion of the dental attachment placement structure of FIG. 17A. In this example, the attachment support 1203 extends indirectly from the frame 1210 via registration the anchor 1201. This configuration can allow the attachment 1202 to be connected to the same tooth that the registration anchor 1201 is registered with. In the example shown, the registration anchor 1201 includes a clearance 1215 to provide proper positioning of the attachment 1202 without interference from the registration anchor 1201 and/or attachment support 1203. The shape and depth of the clearance 1214 may vary depending on the desired tooth position for the attachment 1202. The thickness and height 1214 of the registration anchor 1201, as well as its offset from the tooth, may also vary depending on the desired placement of attachment 1202. In some cases, the clearance 1215 provides access for the treatment professional around the attachment 1202 during, for example, the process of affixing the attachment 1202 to the tooth.

In addition to extending the attachment in a downward or upward direction away from the frame and toward the tooth, the attachment support may also align an attachment surface (e.g., 1230) of the attachment with respect to the tooth surface. In some cases, the attachment support points the attachment surface (e.g., 1230) in a direction toward the midline of the frame. For example, the attachment support may have an arched shape that orients the attachment such that the attachment surface is substantially parallel to the target tooth surface. In other embodiments, the attachment support has an angled shape. This arched or angled shape may also provide room for the user's hand or a detachment tool to access the attachment for detachment as the arched shape can bow outward. The shape and size of the dental attachment 1202 can vary depending on desired force characteristics and the shape and type of corresponding dental appliance (e.g., aligner), as described herein.

In some embodiments, the dental attachment placement structure includes one or more retention supports that extends from the frame and is configured to maintain the dental attachment(s) at the predetermined position(s). FIGS. 17C and 17D illustrate top and bottom perspective views of the dental attachment placement structure of FIG. 17A on a dental arch, showing exemplary retention supports, examples of which are identified as 1206-1, 1206-2 and 1206-3. A retention support can include a contact portion 1212 that is configured to contact one or more teeth and/or gums of the dental arch. In the example shown, the contact portion 1212 is shaped and sized to contact an interproximal region between the teeth. The contact portion can have any shape. In some cases, the contact portion has a substantially spherical shape, as shown. Other non-limiting examples shapes can include a polyhedron (e.g., tetrahedron or cube), cone, cylinder and ovoid shapes. The retention support may include an arched or angled portion that extends the dental contact portion a distance from the frame. For example, the retention support may include a horizontal portion 1209 that extends in a horizontal direction with respect to the frame 1210, and a vertical portion 1207 that extends in a vertical direction with respect to the frame 1210, which position the dental contact portion 1212 on a surface (e.g., lingual surface) of the dental arch.

In some cases, the retention support extends from a different side of the frame than the attachment support. For example, the retention support can extend from a first side of the frame and the attachment support may extend from a second side of the frame. In the example shown in FIGS. 17C and 17D, the retention supports extend from a lingual side of the frame such that the retention supports can contact a lingual portion of the dental arch, and the attachment supports (e.g., 1203) extend from a buccal side of the frame such that the attachments (e.g., 1202) can register at positions on buccal surfaces of the teeth. The retention support can support the lingual side of the frame to stabilize the position of the dental attachment placement structure on the dental arch in three-dimensions.

The frame (e.g., 1210) can be shaped and sized for following at least a portion of the dental arch. In some instances, the frame has an arched shape (e.g., U-shaped) in accordance with the dental arch. In other embodiments, the frame covers only a portion of the dental arch. The frame may be one continuous piece or may include multiple pieces that are joined together. Such sections may have a curved (e.g., arched) shape or be straight and joined together to provide a generally curved (e.g., arched) shape. Although the example shown shows frame 1210 that is adapted to follow along occlusal sides of the teeth (e.g., top of the dental arch), other variations are encompassed by the instant disclosure. For example, the frame may be adapted to follow along the lingual and/or buccal sides of the teeth (e.g. inside of the dental arch and/or outside of the dental arch). In some embodiments the frame is adapted to follow along multiple sides of the teeth (e.g., two or more of the occlusal, lingual and buccal sides). In some cases, the dental attachment placement structure includes more than one frame. For example, two or more frames may be adapted to follow along one or more of the occlusal, lingual and buccal sides of the teeth. Such variations may be included in any of the dental attachment placement structures described herein.

In some embodiments, the registration anchors register with only a subset of the teeth of the dental arch. In some examples, two or more registration anchors are used to span the frame over one or more teeth. For instance, registration anchors 1201-4 and 1201-5 extend from the frame 1210 such that they are separated by a gap portion 1210-1 of the frame. The registration anchors 1201-4 and 1201-5 are configured to register with non-adjacent teeth such that the gap portion 1210-1 of the frame spans teeth 1211-5 and 1211-6. This can allow the gap portion 1210-1 of the frame to suspend over the dental arch and allow dental attachments 1202-5, 1202-6 and retention supports 1206-2, 1206-3, 1206-4 to be positioned over their respective target teeth. This allows the dental attachment placement structure to occlude less of the dental arch than a dental attachment placement structure that covers more tooth surfaces. For instance, the treatment professional can more easily access regions around the intervening teeth 1211-5 and 1211-6 for attaching the attachments 1202-5 and 1202-6.

As described herein, the dental attachment placement structure can be formed using additive manufacturing techniques. In some cases, this involves printing portions of the dental attachment placement structure on a build plate (sometimes referred to as a build platform or base plate) of an additive manufacturing machine without the use of supports. As known, manufacturing supports are often used in 3D printing to support the 3D object on a build plate during the printing process. Such manufacturing supports are typically used to support portions of the 3D object, such as overhangs, that tend to deform during the printing process and are generally removed from the 3D object after the printing process is complete. Such manufacturing supports adds extra material, and adds extra manufacturing time and expense for removing the supports. In some embodiments, the dental attachment placement structure is printed without the use of manufacturing supports, thereby saving material, time and money. In the example shown in FIG. 17C, the frame 1210 can have a surface 1250 (e.g., top or bottom surface) that can be formed on a build plate without the use of manufacturing supports to provide the advantages described above. The surface 1250 may be a substantially flat surface in accordance with a flat build plate surface. The flat surface 1250 may correspond to a top (or bottom) surface of the dental attachment placement structure, where the attachment support(s) (e.g., 1203) and/or retention support(s) (e.g., 1206-1, 1206-2, 1206-3, 1206-4) extend with respect to a bottom (or top) surface of the frame. In some cases, portions of the attachment support(s) and/or retention support(s) can also be built on the build plate and have a correspondingly flat surface.

To use the dental attachment placement apparatus, a treatment professional can position the one or more registration anchors on corresponding tooth surfaces. In the embodiment shown in FIGS. 17A-17D, the registration anchors start at the frame and extend until the anchors encapsulate at least a portion of an incisal edge and extend over one or more sides of corresponding teeth. This positions the one or more dental attachments against corresponding tooth surfaces at predetermined positions. The one or more retention supports can also be positioned on (and in some cases, registered with) surfaces of one or more teeth (e.g., on a lingual side of the dental arch) to maintain the position of the dental attachments. The dental attachment can be affixed to the predetermined position on the tooth surface using, for example, one or more adhesives, as described herein. The dental attachments can be detached from the dental supports such that only the dental attachments from the structure remain coupled to the patient's dental arch.

FIG. 17E illustrate a perspective view of the dental attachment placement structure of FIG. 17A without a dental arch, showing aspects of various contact portions (e.g., 1212-1 and 1212-2) of retention supports. 17F shows a close-up view of a contact portion 1212-3. The contact portion can be configured to be placed in the interproximal region 1255 between adjacent teeth. The contact portion can include one or more conforming surfaces (e.g., 1256-1 and 1256-2) that is configured to conform to the shape of teeth and/or gums. The conformed shape may allow the contact portion to grip onto a surface of the dental arch (e.g., on the lingual side). The shape of the contact portion 1212 can be determined based on virtual model. For instance, a virtual sphere (or cone, tetrahedron, etc.) can be placed in a virtual model of the interproximal region (based on a scan of the patient's dentition) and subtracting regions from the virtual sphere where the teeth would be. In this process, in some embodiments, the gingiva is also taken into account. In some instances, the virtual model of the gingiva can be enlarged by a scaling factor (e.g., making the gingiva 10% larger), and thus any portions of the virtual sphere that are contacting the scaled up gingiva are subtracted from the sphere. In this manner, the contact portion of the retention feature can be formed such that its surfaces will match those of the teeth that it will be in contact with and without interfering with (e.g., contacting) the gingiva, which may cause discomfort to the patient. In some embodiments, the contact portion of the retention feature includes one or more chamfered surfaces (e.g., 1257), e.g., to reduce the amount of protrusion of the contact portion from the dental arch, which may also increase the comfort to the patient.

FIGS. 17G and 17H show alternative views of the dental attachment placement structure of FIG. 17A without the dental attachments and retention supports to allow certain features to be examined and discussed more closely and to aid the reader's understanding. One or more registration anchors (e.g., 1201-1, 1201-2, 1201-3, 1201-4 and 1201-5) can be configured to register with one or more corresponding anchor teeth (e.g., 1215-1, 1215-2, 1215-3, 1215-4, 1215-5 and 1215-6). According to some embodiments, the buccal aspect 1213 (i.e., the tallest point of the buccal surfaces of a tooth) of the one or more anchor teeth can be used as the outermost limit of the dental attachment placement structure. A thickness (e.g., 1280) and width (e.g., 1282) of the frame (or portions of the frame) can be varied such that distance between the frame and the buccal aspect 1213 is as small as practical, thereby minimizing the distance between the frame and the dental arch.

In some embodiments, one or more portions of the dental attachment placement structure is flexible in order to reduce stress concentrations in portions of the structure. Since the dental attachment placement structure may be made of brittle material (e.g., some composite materials), such flexible features can allow the structure to be more resilient and less prone to breakage while still being made of material(s) having desirable properties such as stiffness. The flexible features can reduce the occurrence of breakage during handling (e.g., during manufacture and shipping) of the structure. Having flexible features may allow more structures to be printed (e.g., on a build plate) per 3D printing run. The flexible features may also allow the structures to bend in ways that reduce the dimensions of the structures for more efficient packaging. The flexible features may also provide some tolerance so that the structure can fit on the patient's dental arch more easily. FIGS. 17G-17K show variations of the dental attachment placement structure 17A with various flexible features, in accordance with some embodiments. FIGS. 17G-17K do not show certain features, such as dental attachments and retention supports for simplicity; however, such features can be included.

FIG. 17G illustrates an overhead view of the dental attachment placement structure where a portion 1210-1 of the frame is modified to have a zig-zag or "Z" shape as an alternative to an arch shape. In other variations, the flexible portion can have a sinusoidal or "S" shaped pattern. Such geometries may allow the flexible portion 1210-1 to bend or twist in response to forces (e.g., pushing, pulling, twisting) that may be applied to the frame, thereby distributing the stress and reducing stress concentrations. One or more of portions 1210-1, 1210-2, 1210-3 and 1210-4 of the frame may include such modified curved geometry, depending on particular needs. These types of changes in geometry of the frame allow the frame (or portions thereof) to be flexible without changing the material of the frame. That is, flexible portion 1210-1 may be made of the same material as one or more of portions 1210-2, 1210-3 and 1210-4 of the frame, attachment supports, attachment supports and retention anchors. This solution may be more cost effective than manufacturing the structure with different materials having different degrees of flexibility.

FIGS. 17J and 17K illustrate a link joint alternative to the arch-shaped frame portions of FIG. 17A. The link joint can include interlocking links, such as a first link 1270 and second link 1272 denoted in FIG. 17K. The link joint can include any number of interlocking links (e.g., 2, 3, 4, 5, 6, 10, 20). The interlocking nature of the link joint may allow the links to move with respect to each other while remaining connected with each other. As with a zig-zag or sinusoidal geometry, the link joint geometry can give the frame portion 1210-3 flexibility for resisting breakage when a force (e.g., pushing, pulling, twisting) are applied to the frame. The link joint can be placed anywhere along the frame as needed, including one or more of portions 1210-1, 1210-2, 1210-3 and 1210-4 of the frame. It should be noted that the linked link joint geometry may efficiently be formed using a 3D printing process, whereby the interlocking links can be formed intact (i.e., linked).

The dental attachment placement structure may have flexible portions other than the frame. FIG. 17L illustrates an alternative variation of the structure of FIG. 17A having flexible attachment supports 1203-4, 1203-5 and 1203-6. As opposed an attachment support which tapers from a thicker diameter near the frame to a thinner diameter near the attachment (e.g., 1203-3), the flexible attachment supports may be thinner in diameter and have a sinusoidal or zig-zag shape that provides increased flexibility and resilience in response to an applied force (e.g., pushing, pulling, twisting). Having a more flexible attachment support can also allow for more maneuverability of the attachment (e.g., 1203-4) by the treatment specialist during placement and affixing of the attachment, and may reduce the risk of the attachment support being accidently adhered to the tooth surface. The flexible attachment support can have any shape and is not limited to the sinusoidal or zig-zag shape shown in FIG. 17K. For example, a spring (e.g., spiral), arc, bow or hook shape may also provide a desired amount of flexibility. The dental attachment placement structure can have any number of flexible attachment supports (e.g., 1, 2, 3, 4, 5, 8, 10). In some cases, one or more of the retention supports (e.g., 1206-1) may have a flexible geometry (e.g., sinusoidal or zig-zag shape).

According to some embodiments, the material forming the one or more features of the dental attachment placement structure provides flexibility. FIG. 18 illustrates a perspective view of an example of a lattice structure that can be incorporated into one or more portions of any of the dental attachment placement structures described herein. The lattice structure can include cavities that can increase the flexibility and/or reduces material consumption and weight of the structure. The lattice structure is incorporated into one or more of the frame, registration anchors, attachments, attachment supports, retention supports, or other portion of a dental attachment placement structure. As such, the rigidity or flexibility of the elements can be adjusted based upon the desired implementation.

A dental attachment placement structure may include any combination of the flexible features of FIGS. 17G-17L and 18. For example, the structure can include one or more flexible frame portions 1219 (e.g., FIG. 17I), one or more flexible attachment supports 1221 (e.g., FIG. 17L) and/or one or more flexible retention supports. The number of flexible features can vary depending on particular needs. Generally, the structure may have some flexibility to resist breakage and rigid enough to support and maintain the attachment(s) when placed on a patient's dental arch. In some embodiments, the flexible features are made of the same material as other portions of the structure, as described above. The flexibility may arise, at least in part, due to the shape; e.g., sinusoidal, zig-zag, etc. shapes may be used. In some embodiments, the flexible features are made of a different material (e.g., more flexible) than other portion of the structure.

As described herein, the dental attachment placement structure can be formed based on a virtual model. According to some embodiments, the location and orientation of the frame and other features of the structure are determined based on the location of the dental attachments in the virtual model. FIGS. 17M and 17N illustrate one example of how features of the dental attachment placement structure of FIG. 17A can be formed from a virtual model. The side perspective view of FIG. 17M illustrates a side perspective view of the structure showing how the attachment support 1204-5 that supports attachment 1202-05 can include a base portion 1209-5 and a bridge portion 1209-5. Although not necessary in all embodiments, the base portion 1209-5 can be a solid, extruded, circular structure. The diameter and thickness of the attachment support may vary. The base portion 1209-5 may have a greater thickness (e.g., diameter) than the bridge portion 1208-5.

To determine the location and orientation of the frame 1210, a center of the attachment 1202-3 can be located and projected vertically until it intersects with the plane of the frame 1210. This point can be used as a reference (e.g., correspond to the center of a circle) used to create the base portion 1209-5, thereby informing the location and orientation of the frame 1210. The bridge portion 1209-5 can be formed to connect the base portion 1209-5 to the frame or registration anchor. The dental attachments 1202-4 and 1202-5 can likewise be used to create corresponding base portions and bridge portions for connecting the attachment supports 1204-4 and 1204-5 to the frame or a registration anchor, as well as the remaining dental attachments and attachment supports, until the location and orientation of the entire frame 2101 is determined. During, for example a 3D printing process, the attachment support may be centered under the dental attachment. FIG. 17N illustrates a different view of a base portion 1209 of an attachment support (without the bridge portion) with respect to a corresponding attachment 1202.

Also described herein are dental appliances, e.g., aligners, including one or more mandibular advancement elements. Any of the aligners described herein may include one or more mandibular advancement elements (e.g., mandibular advancement blocks). In some examples, the mandibular advancement element/block may have a stiffness (e.g., Young's modulus) that is greater than that of the more compliant tooth-engagement regions of the aligner. In general, in any of the apparatuses described herein the Young's modulus of the stiffer portion (e.g., the mandibular advancement block) may formed of a material, as described herein, having a Young's modulus of 5 GPa or greater (e.g., 7 GPa or greater, 8 GPa or greater, 9 GPa or greater, 10 GPa or greater, 11 GPa or greater, 12 GPa or greater, 13 GPa or greater, 14 GPa or greater, 15 GPa or greater, 20 GPa or greater, 25 GPa or greater, between 5 GPa and 1000 GPa, etc.). The more compliant regions, such as the tooth-engagement regions, may have a Young's modulus of less than the Young's modulus of the attachment(s), such as a Young's modulus of 10 GPa or less, 9 GPa or less, 8 GPa or less, 7 GPa or less, 6 GPa or less, 5 GPa or less, 4 GPa or less, 3 GPa or less, 2 GPa or less, 1 GPa or less, 0.5 GPa or less, 0.1 GPa or less, etc.). Thus, the tooth-engagement regions of the apparatus may generally have a lower Young's modulus as compared to the stiffer portions (e.g., attachment(s), mandibular advancement block(s), etc.).

Figure 18A:
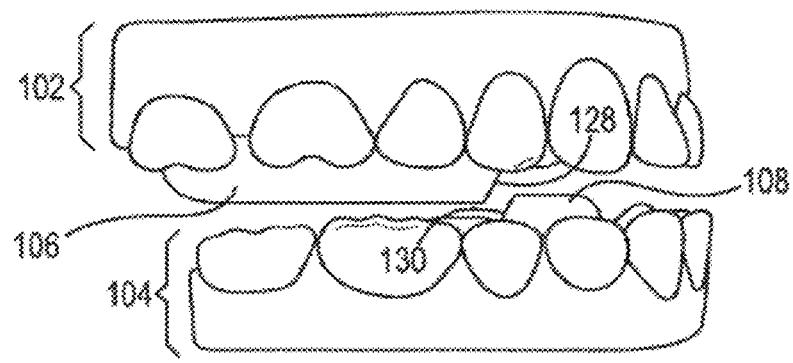
FIGS. 18A-18C illustrate one example of an aligner appliance including mandibular advancement blocks that may be configured as described herein.

Examples of mandibular advancement blocks and appliances including them may be found, for example, in US 20180132975A1, herein incorporated by reference in its entirety. FIG. 18A illustrates a side view of an upper jaw 102 with a first repositioning jaw element 106 and a lower jaw 104 with a second repositioning jaw element 108 according to a number of embodiments of the present disclosure. The upper jaw 102, the first repositioning jaw element 106, the lower jaw 104, and the second repositioning jaw element 108 illustrated in FIG. 18A include virtual images of jaws and repositioning jaw elements, respectively (e.g., virtual jaws and/or virtual repositioning jaw elements), as discussed further herein. The upper jaw 102 can include a maxilla, its related soft and hard tissues, and can include a number of teeth of a patient's upper dentition. The lower jaw 104 can include a mandible, its related soft and hard tissues, and can include a number of teeth of the patient's lower dentition.

In some instances, the patient may exhibit abnormal occlusion or malocclusion. For instance, this may include a jaw (or both) that is protrusive, retrusive, or laterally displaced. As an example, positioning of the number of teeth of the patient's upper dentition and the number of teeth of the patient's lower dentition can be such that the best fit of the upper dentition with the lower dentition results in a misalignment of the lower jaw 104 relative to the upper jaw 102 either in positional relations or at the level of the jaw joint which connects the lower jaw 104 to the upper jaw 102. The lower jaw 104 can be in a retruded position, for instance, resulting in a distance (e.g., space) between the front teeth of the upper dentition and the front teeth of the lower dentition (e.g., an increased overjet). Correction of the malocclusion can be beneficial to the patient in terms of improved chewing ability, reduced premature wear of the teeth, and/or improved facial aesthetics.

In some embodiments, the upper jaw 102 and lower jaw 104 illustrated in FIG. 18A can include a virtual model of the patient's upper jaw and lower jaw. A virtual model of one or more dental appliances (e.g., an appliance for the upper dentition and an appliance for the lower dentition which may also be connected together) each having a shell configured to reposition a number of teeth of the patient can be provided. The virtual model of the dental appliance can include a virtual model of a dental appliance configured to reposition the number of teeth of the patient.

Repositioning jaw elements can be positioned on occlusal, buccal, and/or lingual surfaces of a dental appliance to be placed over the patient's teeth. A repositioning jaw element, as used herein, can include a portion of material (e.g., a geometric shaped element, such as a block shape) extending from a surface of the shell of the appliance, as discussed further herein. For instance, a virtual repositioning jaw element can be positioned on the shell of the virtual model of the dental appliance parallel to a bite plane of the patient. A bite plane, as used herein, can include a surface from the incisal edges of the incisors and the tips of the occluding surfaces of the posterior teeth that is a mean of the curvature of the surface.

In some embodiments, the position of the virtual repositioning jaw element can be revised to align with a midline (e.g., middle) of at least one tooth of the number of teeth wherein the virtual repositioning jaw element extends from a surface of the shell of the virtual model of the dental appliance. However, embodiments in accordance with the present disclosure are not so limited and the virtual repositioning jaw elements may not be aligned with a midline of the at least one tooth in various embodiments. The virtual model of the dental appliance, including the virtual repositioning jaw element, can be used to determine a treatment plan for the patient and/or to form a physical dental appliance and/or physical repositioning jaw element (e.g., as discussed further herein).

The physical repositioning jaw element can be formed of a variety of material types. In some embodiments, the physical repositioning jaw element can be formed of the same material as the shell of the dental appliance (e.g., a polymeric material). For instance, the physical repositioning jaw element can be formed integrally with the shell and/or formed of a same material as the shell.

The repositioning jaw elements can also be positioned in different places, in some embodiments. For example, the first repositioning jaw element 106 and the second repositioning jaw element 108 can be positioned near occlusal surfaces of the teeth of the patient to advance the placement of the lower jaw 104 in a forward direction (e.g., in an anterior direction and/or toward a patient's lips) or in a backward direction (e.g., in a posterior direction and/or towards the back of the patient's head). For instance, occlusal surfaces of teeth of the upper jaw 102 and lower jaw 104 can be separated using the first repositioning jaw element 106 and the second repositioning jaw element 108 to move (e.g., to move sagittally) the lower jaw 104 of the patient from an articulation path during opening (e.g., the path that the jaw currently follows when opening) to a desired range of jaw opening extending from an advanced or forward position of occlusion, as described further herein. As an example, the first repositioning jaw element 106 can include a first surface 128 and the second repositioning jaw element 108 can include a second surface 130 to interface, interact, and/or otherwise engage with the first surface 128 of the first repositioning jaw element 106, as discussed further herein. By moving the lower jaw 104, muscles associated with movement of the lower jaw 104 can be retrained to a new position (generally in a forward and/or downward direction, or in a backward direction) or the lower jaw may be permitted to grow more fully if the patient has not fully developed skeletally.

Figure 18B:
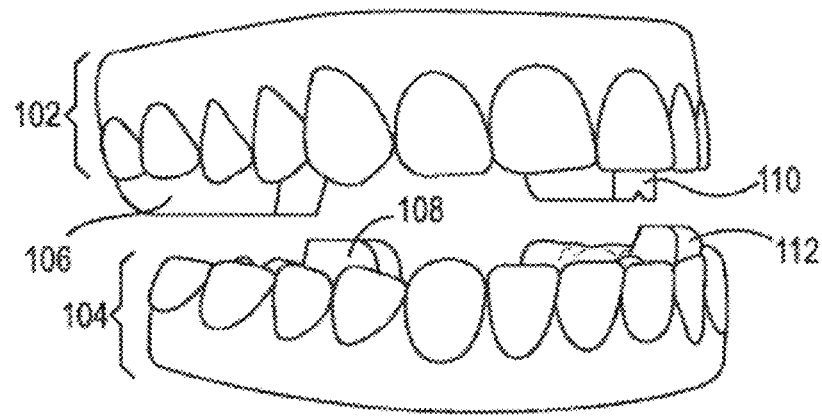

FIG. 18B illustrates a front view of an upper jaw 102 with a first repositioning jaw element 106 and a third repositioning jaw element 110 and a lower jaw 104 with a second repositioning jaw element 108 and a fourth repositioning jaw element 112 according to a number of embodiments of the present disclosure. A front view, as used herein, can include an anterior view and/or a more anterior view of the jaws as compared to a side view. The upper jaw 102, the first repositioning jaw element 106, the third repositioning jaw element 110, the lower jaw 104, the second repositioning jaw element 108, and the fourth repositioning jaw element 112 illustrated in FIG. 18B can include virtual images of jaws and repositioning jaw elements, respectively (e.g., virtual jaws and/or virtual repositioning jaw elements), as discussed further herein. As illustrated by FIG. 18B, two repositioning jaw elements (e.g., the first repositioning jaw element 106 and the third repositioning jaw element 110) can be positioned near (e.g., adjacent to) occlusal surfaces of the upper jaw 102 and two repositioning jaw elements (e.g., the second repositioning jaw element 108 and the fourth repositioning jaw element 112) can be positioned near occlusal surfaces of the lower jaw 104.

The first repositioning jaw element 106 can be positioned near the occlusal surfaces of the posterior teeth (in the embodiment illustrated by FIG. 18B, the molars and/or bicuspids) of the upper jaw 102 and the second repositioning element 108 can be positioned near the occlusal surfaces of the posterior teeth (in the embodiment illustrated by FIG. 18B, the bicuspids) of the lower jaw 104. The first repositioning jaw element 106 and second repositioning jaw element 108 can be located near a first posterior side of the patient's dentition.

The first repositioning jaw element 106 and the second repositioning jaw element 108 can include surfaces that can interface, interact, and/or engage with a surface of a repositioning jaw element on a shell of an opposing jaw. For instance, a first surface of the first repositioning jaw element 106 can interface, interact, and/or engage with a second surface of the second repositioning jaw element 108. A surface, as used herein, can include a side and/or end surface of a repositioning jaw element. In some embodiments, the first surface can include a slanted surface on a mesial-facing surface of the first repositioning jaw element 106 and/or the second surface can include a slanted surface on a distal-facing surface of the second repositioning jaw element 108, for instance. For example, a mesial-facing surface can include a surface of a repositioning jaw element that is in a direction toward the anterior midline of the teeth. A distal-facing surface can include a surface of a repositioning jaw element that is in a direction toward the last tooth in each quadrant of a dental arch. However, embodiments in accordance with the present disclosure are not so limited. A mesial-facing surface, in some embodiments, can be facing toward the facial plane (e.g., normal to the facial plane), whereas a distal-facing surface can be facing away from the facial plane (e.g., normal to the facial plane but in the opposite direction). The surfaces of the repositioning jaw elements, in accordance with embodiments of the present disclosure, can be oriented in a variety of directions.

The third repositioning jaw element 110 can be positioned near the occlusal surfaces of the posterior teeth (in embodiment illustrated by FIG. 18B, molars and/or bicuspids) of the upper jaw 102 and the fourth repositioning jaw element 112 can be positioned near the occlusal surfaces of the posterior teeth (in the embodiment illustrated by FIG. 18B, bicuspids) of the lower jaw 104. The third repositioning jaw element 110 and the fourth repositioning jaw element 112 can be located near a second posterior side of the patient's dentition. The third repositioning jaw element 110 and the fourth repositioning jaw element 112 can include surfaces that can interface, interact, and/or engage with a surface of a repositioning jaw element on an opposite jaw. For instance, a third surface of the third repositioning jaw element 110 can interface, interact, and/or engage with a fourth surface of the fourth repositioning jaw element 112. The third surface can include a slanted surface on a mesial-facing surface of the third repositioning jaw element 110 and the fourth surface can include a slanted surface on a distal-facing surface of the fourth repositioning jaw element 112, for instance.

However, embodiments in accordance with the present disclosure are not so limited. For instance, the surfaces of the repositioning jaw elements 106, 108, 110, 112 can be oriented in a variety of directions. For instance, the first surface of the first repositioning jaw element 106 and the third surface of the third repositioning jaw element 110 can include distal-facing slanted surfaces and/or the second surface of the second repositioning jaw element 108 and the fourth surface of the fourth repositioning jaw element 112 can include mesial-facing slanted surfaces, among other orientations.

The surfaces (e.g., that interact and/or interface) of the repositioning jaw elements 106, 108, 110, 112 can be angled, in various embodiments, to guide the lower jaw 104 into position and gain desired lateral or prevent unwanted lateral movement. The surfaces can be angled in buccal-lingual and/or mesial-distal direction, for example. The angle of interacting and/or interfacing surfaces (e.g., two surfaces that are designed to interface, interact, and/or engage with each other either actively or passively) can have the same degree and/or slant or a different degree and/or slant (e.g., as illustrated by the embodiment of FIGS. 14A-14B).

For example, the first surface of the first repositioning jaw element 106 and the second surface of the second repositioning jaw element 108 can interface at a first slant. The slant can include, for instance, a degree of angle of the repositioning jaw elements. The third surface of the third repositioning jaw element 110 and the fourth surface of the fourth repositioning jaw element 112 can interface at a second slant.

The first slant and the second slant, in accordance with a number of embodiments, can include opposing angles. The opposing angles of slants on opposing posterior sides of the patient's dentition can facilitate desired lateral movement or limit and/or prevent unwanted lateral movement. In some embodiments, the sum of the opposing angles can include 180 degrees. As an example, if the first slant is 70 degrees then the second slant can include 110 degrees.

In accordance with some embodiments, the repositioning jaw elements 106, 108, 110, 112 extending from surfaces of a shell can be used to generate distalizing force on at least some of the teeth that are located within the shell. For example, when the repositioning jaw elements 106, 108, 110, 112 interface, the distalizing forces can be isolated to posterior teeth of the upper jaw. The distalizing forces can, in some embodiments, cause tooth movement of the upper jaw posterior teeth in a distal direction. As such, the repositioning jaw elements 106, 108, 110, 112 in various embodiments can be a substitute for Class II elastics.

In some embodiments, the repositioning jaw elements 106, 108, 110, 112 can include geometric features to engage with a repositioning jaw element on an opposing jaw. Geometric features, as used herein, can include a variety of protruding geometric shapes (e.g., cylinder, rectangular, etc.) and/or receding geometric shapes (e.g., negative space that matches the protruding geometric shape on a repositioning jaw element on an opposing jaw, as illustrated in the embodiment of FIG. 8A). For example, a geometric feature on the first surface of the first repositioning jaw element 106 can include a convex cylindrical shaped feature and a geometric feature on the second surface of the second repositioning jaw element 108 can include a concave cylindrical shaped feature shaped to mate with the geometric feature on the first surface of the first repositioning jaw element 106

Figure 19A:
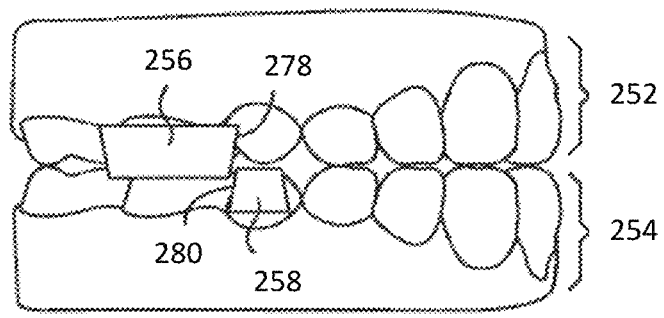
FIGS. 19A-19B illustrate examples of an aligner appliance including mandibular advancement blocks that may be configured as described herein.

FIG. 19A illustrates a side view of an upper jaw 252 with a first repositioning jaw element 256 and a lower jaw 254 with a second repositioning jaw element 258 according to a number of embodiments of the present disclosure. The upper jaw 252, the first repositioning jaw element 256, the lower jaw 254, and the second repositioning jaw element 258 illustrated in FIG. 19A can include virtual images of jaws and repositioning jaw elements, respectively (e.g., virtual jaws and/or virtual repositioning jaw elements), as discussed further herein. As illustrated in the embodiment of FIG. 19A, the first repositioning jaw element 256 can be positioned near a buccal surface of the posterior teeth (e.g., molars and bicuspids) of the upper jaw 252 of the patient to move the position (e.g., to move sagittally) of the lower jaw 254 in a forward direction or backward direction.

Although not illustrated in FIG. 19A, the first repositioning jaw element 256 can extend from a buccal surface of a first shell of a dental appliance. A buccal surface of a shell, as used herein, can include an exterior surface of a shell near the buccal surface of the teeth therein. Further, in various embodiments, the first repositioning jaw element 256 can be positioned near a lingual surface of the first shell. A lingual surface of a shell can include an exterior surface of the shell near the lingual surface of the teeth therein.

The second repositioning jaw element 258 can be positioned near a buccal surface of the posterior teeth (e.g., bicuspids) of the lower jaw 254 of the patient to move the position of the lower jaw 254 in a forward direction or backward direction. Although not illustrated in FIG. 19A, the second repositioning jaw element 258 can extend from a buccal surface of a second shell of a dental appliance.

The first repositioning jaw element 256 and the second repositioning jaw element 258 can interface. For instance, a first surface 278 of the first repositioning jaw element 256 can interface with a second surface 280 of the second repositioning jaw element 258. The first repositioning jaw element 256 and the second repositioning jaw element 258 can be positioned to interface in a presence of a temporary bite (e.g., a fully engaged sagittal jaw position of the patient's upper dentition and the patient's lower dentition) in a manner to reposition the patient's jaw. A fully engaged sagittal jaw position, as previously discussed, can include a relationship of the mandible and the maxilla when the upper and lower jaw are closed as far as the dental appliance with the repositioning jaw elements will allow (e.g., a partial occlusal jaw position).

For example, the first surface 278 of the first repositioning jaw element 256 interfacing with the second surface 280 of the second repositioning jaw element 258 can place a force on the patient's jaw to reposition the patient's jaw. The force can, for instance, sagittally move the patient's lower jaw 254.

In various embodiments, at least one of the repositioning jaw elements 256, 258 can extend past an occlusal plane of the upper jaw 252 and/or lower jaw 254 of the patient. For example, the first repositioning jaw element 256 can extend past the occlusal plane of the upper jaw 252 to interface with the second repositioning jaw element 258. The second repositioning jaw element 258 may not extend past the occlusal plane of the lower jaw 254, for instance. Alternatively, the second repositioning jaw element 258 can extend past the occlusal plane of the lower jaw 254 to interface with the first repositioning jaw element 256 and the first repositioning jaw element 256 may not extend past the occlusal plane of the upper jaw 252. Further, in some embodiments, both the first repositioning jaw element 256 and the second repositioning jaw element 258 can extend past the occlusal plane of the upper jaw 252 and the lower jaw 254, respectively, to interface with one another.

Figure 19B:
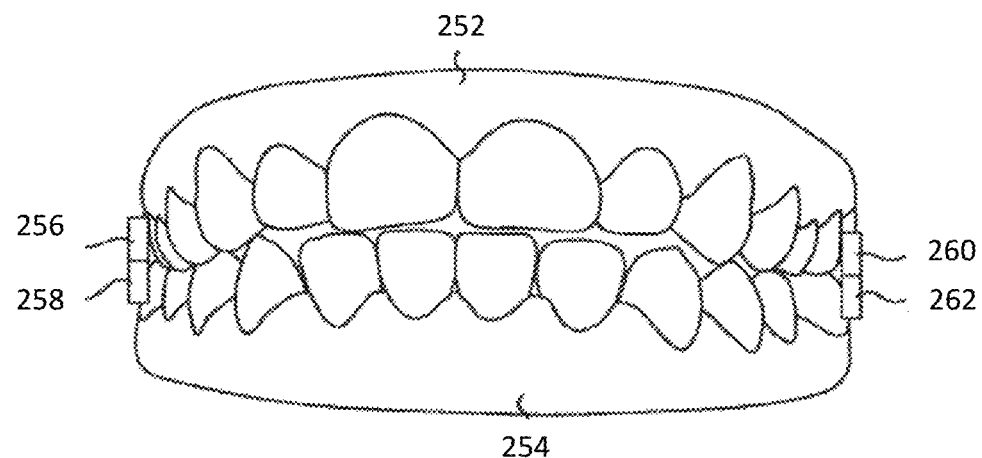

FIG. 19B illustrates a front view of an upper jaw 252 with a first repositioning jaw element 256 and a third repositioning jaw element 260 and a lower jaw 254 with a second repositioning jaw element 258 and a fourth repositioning jaw element 262 according to a number of embodiments of the present disclosure. The upper jaw 252, the first repositioning jaw element 256, the third repositioning jaw element 260, the lower jaw 254, the second repositioning jaw element 258, and the fourth repositioning jaw element 262 illustrated in FIG. 19B can include virtual images of jaws and repositioning jaw elements, respectively (e.g., virtual jaws and/or virtual repositioning jaw elements), as discussed further herein. As illustrated by FIG. 19B, two repositioning jaw elements (e.g., the first repositioning jaw element 256 and the third repositioning jaw element 260) can be positioned near buccal surfaces of the upper jaw 252 and two repositioning jaw elements (e.g., the second repositioning jaw element 258 and the fourth repositioning jaw element 262) can be positioned near buccal surfaces of the lower jaw 254.

For example, the first repositioning jaw element 256 can be positioned near the buccal surfaces of posterior teeth (e.g., molars and/or bicuspids) of the upper jaw 252 and the second repositioning jaw element 258 can be positioned near the buccal surfaces of posterior teeth (e.g., bicuspids) of the lower jaw 254. The first repositioning jaw element 256 and the second repositioning jaw element 258 can be located near a first posterior side of the patient's dentition (e.g., positioned on a first posterior side of a first shell and a second shell).

The first repositioning jaw element 256 and the second repositioning jaw element 258 can include surfaces designed to interact, interface, and/or otherwise engage with one another. For instance, a first surface of the first repositioning jaw element 256 can interface with a second surface of a second repositioning jaw element 258. The first surface can include a slanted surface on a mesial-facing surface of the first repositioning jaw element 256 and the second surface can include a slanted surface on a distal-facing surface of the first repositioning jaw element 258, for example.

The third repositioning jaw element 260 can be positioned near the buccal surfaces of posterior teeth (e.g., molars and/or bicuspids) of the upper jaw 252 and the fourth repositioning jaw element 262 can be positioned near the buccal surfaces of posterior teeth (e.g., bicuspids) of the lower jaw 254. The third repositioning jaw element 260 and the fourth repositioning jaw element 262 can be located near a second posterior side of the patient's dentition (e.g., positioned on a second posterior side of a shell of a first shell and a second shell).

The third repositioning jaw element 260 and the fourth repositioning jaw element 262 can include surfaces designed to interact, interface, and/or otherwise engage with one another. For instance, a third surface of the third repositioning jaw element 260 can interface with a fourth surface of the fourth repositioning jaw element 262. The third surface can include a slanted surface on a mesial-facing surface of the third repositioning jaw element 260 and the fourth surface can include a slanted surface on a distal-facing surface of the fourth repositioning jaw element 262, for example.

The surfaces of the repositioning jaw elements 256, 258, 260, 262 can be angled, in various embodiments, to guide the lower jaw 254 into the intended and/or final jaw position and/or prevent unwanted lateral movement. The surfaces can be angled in buccal-lingual and/or mesial-distal direction. The angle of the surfaces (e.g., two surfaces that are designed to interface) can be comprised of supplemental angles (e.g., have the same slants at the interface).

For example, the first surface of the first repositioning jaw element 256 and the second surface of the second repositioning jaw element 258 can interface at a first slant. The third surface of the third repositioning jaw element 260 and the fourth surface of the fourth repositioning jaw element 262 can interface at a second slant.

Although not illustrated by the embodiments of FIG. 19B, the first repositioning jaw element 256 can extend from a buccal surface of a first shell of a dental appliance and/or the second repositioning jaw element 258 can extend from a buccal surface of a second shell of the dental appliance. The first repositioning jaw element 256 and the second repositioning jaw element 258 can be located near a first side of the patient's dentition (e.g., the right side of the patient's dentition). The third repositioning jaw element 260 can extend from a buccal surface of the first shell of the dental appliance and the fourth repositioning jaw element 262 can extend from a buccal surface of the second shell of the dental appliance. The third repositioning jaw element 260 and the fourth repositioning jaw element 262 can be located near a second side of the patient's dentition (e.g., a left side of the patient's dentition).

Figure 18C:
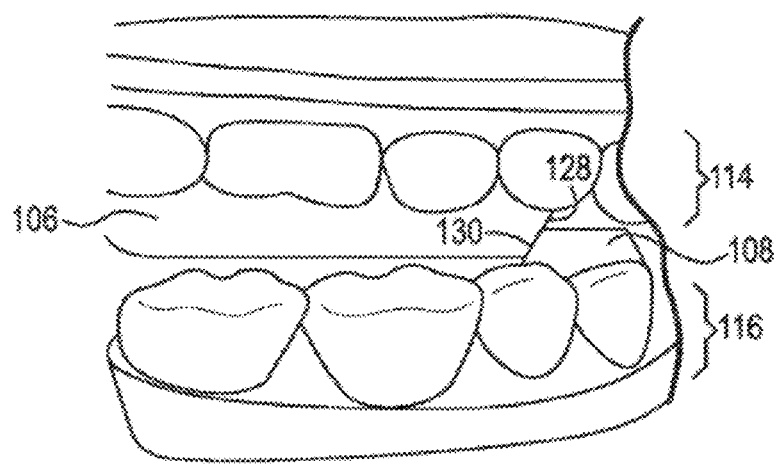

FIG. 18C illustrates a side view of a first shell 114 with a first repositioning jaw element 106 and a second shell 116 with a second repositioning jaw element 108 according to a number of embodiments of the present disclosure. The side view can, for instance, include a profile view of the first shell 114 and the second shell 116. The first shell 114 and the second shell 116, in some embodiments, can include a removable dental appliance.

Other examples of aligners including features that may be formed to be more rigid than tooth-engagement regions may include apparatuses with an occlusal block, such as those described in US20210169617, incorporated herein by reference in its entirety.

In general, any of the aligners described herein may have variable properties, including a mix of regions of different stiffness/compliances (e.g., Young's modulus). For example, the methods and features described herein may be used with and/or may modify the apparatuses shown and described in US20170007359A1, herein incorporated by reference in its entirety. For example, the methods described herein may be used to make any of the dental appliances shown and described in the in US20170007359A1.

Typically, the example described above may be implemented by changing the resin partway during the manufacturing process (additive manufacturing process) as mentioned. Alternatively, a hybrid polymer may be used, in which different components or compositions within a layer may be used.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-junctionally employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of forming a palatal expander to be worn by a patient to expand a palatal arch of the patient, the method comprising:

accessing a three-dimensional (3D) model that is based on the patient's upper dental arch;

based on the 3D model, 3D printing a patient-specific palatal region made of a first polymer material by photopolymerizing a first photo-curable material in a 3D printing vat, wherein the palatal region is shaped and sized to apply an expansion force across the patient's palate, and wherein the palatal region is formed at a first location in the 3D printing vat;

removing the first photo-curable material from the vat;

adding a second photo-curable material in the vat, the second photo-curable material being different than the first photo-curable material;

based on the 3D model, 3D printing a patient-specific left tooth engagement region configured to receive one or more teeth of a left side of an upper jaw of the patient and a patient-specific right tooth engagement region configured to receive one or more teeth of a right side of the upper jaw of the patient, each made of a second polymer material that is less rigid than the first polymer material by photopolymerizing the second photo-curable material in the vat, wherein the left tooth engagement reion and the right tooth engagement region are formed at second and third locations that are on left and right sides, respectively, of the first location in the 3D printing vat;

removing the second photo-curable material from the vat; and forming, with the palatal region and the left and right tooth engagement regions in place at their respective locations, a left junction region that directly couples the palatal region to the left tooth engagement region and a right junction region that directly couples the palatal region to the right tooth engagement region, wherein each of the left and right junction regions is formed by:

sequentially adding and removing different mixtures to and from the vat, wherein each mixture added to the vat has a different ratio of the first and second photo-curable materials than a mixture added previously to the vat; and sequentially 3D printing different portions of the corresponding left or right junction region by photopolymerizing each of the different mixtures in the vat following each respective addition, wherein each portion of the different portions of the corresponding left or right junction region is made of a different combination of the first and second polymer materials based on the different ratios of the first and second photo-curable materials in the vat, thereby sequentially photopolymerizing multiple layers to form the corresponding left or right junction region in a layer by layer fashion such that each layer has a different ratio of the first and second polymer materials, thereby providing gradual material transitions between the palatal region and each of the left and right tooth engagement regions and a robust bond between the palatal region and each of the left and right tooth engagement regions.

2. The method of claim 1, further comprising determining a relative shrinkage factor associated with the first and second polymer materials, and adjusting at least one 3D model for forming the palatal region or the left and right tooth engagement regions based on the relative shrinkage factor.

3. The method of claim 1, wherein the first polymer material is a composite polymer material including fibers or metal material integrated therein.

4. The method of claim 1, wherein the left and right junction regions are configured to distribute the expansion force over a lingual portion of each of the corresponding left or right tooth engagement regions that is configured to contact gums or a region more distal from an occlusal surface of the patient's teeth.

5. The method of claim 1, wherein each of the left and right tooth engagement regions includes one or more attachment cavities that are configured to engage with attachments bonded to the patient's teeth.

6. The method of claim 1, wherein each of the left and right tooth engagement regions includes a removal feature extending from a buccal side of the corresponding left or right tooth engagement region, the removal feature adapted to facilitate removal of the palatal expander from the patient's teeth.

7. The method of claim 1, wherein the different mixtures are liquid mixtures of monomer and/or oligomer forms of the first and second polymer materials.

8. The method of claim 1, wherein each of the left and right tooth engagement regions includes one or more attachment cavities that are shaped for engagement with attachments bonded to the patient's teeth.

9. The method of claim 1, wherein each of the left and right tooth engagement regions includes a removal feature extending from a buccal side of the corresponding left or right tooth engagement region.

10. The method of claim 1, wherein a rigidity of the each of the left and right junction region varies based on the different ratios of the first and second photo-curable materials.

11. The method of claim 1, wherein forming each of the left and right junction regions comprises forming a gradient change in a ratio of the first polymer material relative to the second polymer material across the corresponding left or right junction region from the palatal region toward the corresponding left or right tooth engagement region.

12. A method of forming a palatal expander to be worn by a patient to expand a palatal arch of the patient, the method comprising:

accessing a three-dimensional (3D) model that is based on the patient's upper dental arch;

based on the 3D model, 3D printing a patient-specific palatal region made of a first polymer material by photopolymerizing a first photo-curable material in a 3D printing vat, wherein the palatal region is shaped and sized to apply an expansion force across the patient's palate, and wherein the palatal region is formed at a first location in the 3D printing vat;

removing the first photo-curable material from the vat;

removing the second photo-curable material in the vat, the second photo-curable material being different than the first photo-curable material;

based on the 3D printing a patient-specific left tooth engagement region configured to receive one or more teeth of a left side of an upper jaw of the patient and a patient-specific right tooth engagement region configured to receive one or more teeth of a right side of the upper jaw of the patient, each made of a second polymer material by photopolymerizing the second photo-curable material in the vat, the second polymer material being less rigid than the first polymer material, wherein the left tooth engagement region and the right tooth engagement region are formed at second and third locations that are on left and right sides, respectively, of the first location in the 3D printing vat; and forming, with the palatal region and the left and right tooth engagement regions in place at their respective locations a left junction region that directly couples the palatal region to the left tooth engagement region and a right junction region that directly couples the patient-specific palatal region to the right tooth engagement region, the left and right junction regions each including a gradient change in a ratio of the first polymer material relative to the second polymer material across each of the left and right junction region from the palatal region toward the corresponding left or right tooth engagement region to provide a robust bond between the palatal region and each of the left and right tooth engagement regions, wherein forming each of the left and right junction regions comprises:

sequentially adding and removing different mixtures to and from the vat, wherein each mixture added to the vat has a different ratio of the first and second photo-curable materials than a mixture added previously to the vat; and forming different portions of the corresponding left or right junction region by sequentially photopolymerizing the different mixtures in the vat following each respective addition, wherein each portion of the different portions of the corresponding left or right junction region is made of a different combination of the first and second polymer materials based on the different ratios of the first and second photo-curable materials in the vat, thereby sequentially photopolymerizing multiple layers to form the corresponding left or right junction region in a layer by layer fashion such that each layer has the different combination of the first and second polymer materials.

13. The method of claim 12, further comprising determining a relative shrinkage factor associated with the first and second polymer materials, and adjusting at least one 3D model for forming the palatal region or the left and right tooth engagement regions based on the relative shrinkage factor.

14. A method of forming a palatal expander to be worn by a patient to expand a palatal arch of the patient, the method comprising:

accessing a three-dimensional (3D) model that is based on the patient's upper dental arch;

based on the 3D model, 3D printing a patient-specific left tooth engagement region made of a first polymer material by photopolymerizing a first photo-curable material in a 3D printing vat, wherein the left tooth engagement region has one or more cavities shaped to accommodate one or more corresponding teeth of a left side of an upper jaw of the patient, wherein the left tooth engagement region is formed at a first location in the 3D printing vat;

removing the first photo-curable material from the vat and adding a first set of different mixtures of the first photocurable material and a second photo-curable material in the vat, wherein the second photo-curable material is different than that first photo-curable material;

based on the 3D model, 3D printing a left junction region that directly couples to the left tooth engagement region using the first set of different mixtures of the first photo-curable material and the second photo-curable material in the vat, wherein the left junction region is formed in a second location within the vat that is different than the first location;

removing a last mixture of the first set of different mixtures of the first and second photo-curable materials from the vat and adding the second photo-curable material in the vat;

based on the 3D model, 3D printing a patient-specific palatal region that is directly coupled to the left junction region, the palatal region made of a second polymer material by photopolymerizing the second photo-curable material in the vat, wherein the palatal region is shaped and sized to apply an expansion force across the patient's palate, wherein the palatal region is formed at a third location in the 3D printing vat that is different than the first and second locations;

removing the second photo-curable material from the vat and adding a second set of different mixtures of the first photo-curable material and the second photo-curable material in the vat;

based on the 3D mode, 3D printing a right junction region that is directly coupled to the palatal region using a second set of different mixtures of the first and second photo-curable materials in the vat, wherein the right junction region is formed in a fourth location of the vat that is different than the first, second and third locations;

removing a last mixture of the second set of different mixtures of the first and second photo-curable materials from the vat and adding the first photo-curable material in the vat; and based on the 3D model, 3D printing a right tooth engagement region that is directly coupled to the right junction region, the right tooth engagement region made of the first polymer material by photopolymerizing the first photo-curable material in the vat, wherein the right tooth engagement region has one or more cavities shaped to accommodate one or more corresponding teeth of a right side of the upper jaw of the patient, wherein the right tooth engagement region is formed in a fifth location of the vat that is different than the first, second, third and fourth locations;

wherein forming each of the left and right junction regions comprises:

sequentially adding and removing each different mixture of the respective first or second different mixtures to and from the vat, wherein each different mixture added to the vat has a different ratio of the first and second photo-curable materials than a mixture added previously to the vat; and sequentially forming different portions of the corresponding left or right junction region by photopolymerizing each of the different mixtures in the vat following each respective addition, wherein each portion of the different portions of the corresponding left and right junction region is made of a different combination of the first and second polymer materials based on the different ratios of the first and second photo-curable materials in the vat, thereby sequentially photopolymerizing multiple layers to form the corresponding left or right junction region in a layer by layer fashion such that each layer of the right junction region has the different combination of the first and second polymer materials, thereby providing gradual material transitions between palatal region and each of the left and right tooth engagement regions and a robust bond between the palatal region and each of the left and right tooth engagement regions.

15. The method of claim 14, wherein forming each of the left and right junction regions comprises forming a gradient change in a ratio of the first polymer material relative to the second polymer material across the corresponding left or right junction region from the palatal region toward the corresponding left or right tooth engagement region.

* * * * *